(12) United States Patent
Bensimon et al.

(10) Patent No.: US 9,915,655 B2
(45) Date of Patent: Mar. 13, 2018

(54) PROCESS FOR DETECTION OF DNA MODIFICATIONS AND PROTEIN BINDING BY A SINGLE MOLECULE MANIPULATION

(71) Applicants: CENTRE NATIONAL DE LA RECHERCHE SCIENTIFIQUE (CNRS), Paris (FR); ECOLE NORMALE SUPERIEURE, Paris (FR); UNIVERSITE PIERRE ET MARIE CURIE (PARIS 6), Paris (FR)

(72) Inventors: David Bensimon, Paris (FR); Vincent Croquette, Antony (FR); Harold Gouet, Paris (FR); Jean-Francois Allemand, Bourg la Reine (FR); Fang-Yuan Ding, Alhambra, CA (US)

(73) Assignees: CENTRE NATIONAL DE LA RECHERCHE SCIENTIFIQUE (CNRS), Paris (FR); ECOLE NORMALE SUPERIEURE, Paris (FR); UNIVERSITE PIERRE ET MARIE CURIE (PARIS 6), Paris (FR)

( * ) Notice: Subject to any disclaimer, the term of this patent is extended or adjusted under 35 U.S.C. 154(b) by 0 days.

(21) Appl. No.: 14/761,944

(22) PCT Filed: Jan. 22, 2014

(86) PCT No.: PCT/EP2014/051272
§ 371 (c)(1),
(2) Date: Jul. 18, 2015

(87) PCT Pub. No.: WO2014/114687
PCT Pub. Date: Jul. 31, 2014

(65) Prior Publication Data
US 2015/0362488 A1 Dec. 17, 2015

(30) Foreign Application Priority Data
Jan. 22, 2013 (EP) .................................... 13305074

(51) Int. Cl.
*C12Q 1/68* (2006.01)
*C12P 19/34* (2006.01)
*G01N 33/557* (2006.01)

(52) U.S. Cl.
CPC ......... *G01N 33/557* (2013.01); *C12Q 1/6883* (2013.01); *C12Q 2600/154* (2013.01); *C12Q 2600/156* (2013.01)

(58) Field of Classification Search
None
See application file for complete search history.

(56) References Cited

U.S. PATENT DOCUMENTS 7,052,650 B2   5/2006   Strick et al.
7,244,391 B2   7/2007   Strick et al.

FOREIGN PATENT DOCUMENTS

EP   146 815 B1   7/1985
EP   152 886 A2   8/1985
(Continued)

OTHER PUBLICATIONS

Manosas et al. Nat Chem Biol. 2009. 5(12):904-912.*
(Continued)

*Primary Examiner* — Joseph G. Dauner
(74) *Attorney, Agent, or Firm* — Arrigo, Lee & Guttman LLP

(57) ABSTRACT

The present invention relates to a method for determining whether a protein binds to a specific DNA sequence. This method is useful in particular for identifying modifications to the DNA sequence (e.g. methylations) via the binding of proteins that specifically recognize those modifications (e.g. antibodies), but also to identify the binding sequence on DNA of a variety of proteins.

15 Claims, 13 Drawing Sheets
(4 of 13 Drawing Sheet(s) Filed in Color)

(56) References Cited

FOREIGN PATENT DOCUMENTS

| | | | |
|---|---|---|---|
| EP | 329 198 | B1 | 8/1989 |
| EP | 2 390 351 | A1 | 11/2011 |
| EP | 2390351 | A1 | 11/2011 |
| WO | 92/16659 | A1 | 10/1992 |
| WO | 2011/147929 | A1 | 12/2011 |
| WO | 2011/147931 | A1 | 12/2011 |

OTHER PUBLICATIONS

Blackwell et al. The Journal of Biological Chemistry. 1998. 273(48):32049-32054.*
Genschel et al. Journal of Biological Chemistry. 1998. 273(31):19895-19901.*
Taira et al. Mutation Research. 2008. 640:107-112.*
Tachiki et al. The Journal of Biological Chemistry. 2000. 275(52):40703-40709.*
Lamers et al. Nature. 2000. 407:711-717.*
Jin et al. Nucleic Acids Research. 2010. 38(11):e125.*
Kurita et al. Anal. Chem. 2012. 84:7533-7538.*
Maria Manosas et al., Ccoupling DNA unwiding activity with primer synthesis in the bacteriophage T4 primosome, Nature chemical biology, vol. 5, N°12, 2009, pp. 904-912.
Maria Manosas et al ., Coupling DNA unwiding activity with primer synthesis in the bacteriophage T4 primosome : supplementary information, Nature chemical biology, vol. 5, N°12, 2009, pp. 1-21.
Jaya G. Yodh et al, Insight into helicase mechanism and function revealed through single-molecule approaches, Quarterly reviews of biophysics, vol. 43, N°02, pp. 185-217, 2010.
The Encode Project Consortium, An integrated encyclopedia of DNA elements in the human genome, Nature, vol. 489, N°7414, Sep. 2012, pp. 57-74.
Ito et al., Role of Tet proteins in 5mC to 5hmC conversion, ES cell selfrenewal, and ICM specification, Nature, 466: 1129-1133, 2010.
Ko et al., Impaired hydroxylation of 5-methylcytosine in myeloid cancers with mutant TET2, Nature, 468: 839-843, 2010.
Szulwach et al., 5-hmC—mediated epigenetic dynamics during postnatal neurodevelopment and aging,Nature Neurosci, 14: 1607-1611, 2011.
Haffner et al., Global 5-hydroxymethylcytosine content is significantly reduced in tissue stem/progenitor cell compartments and in human cancers, Oncotarget, 2: 627-637, 2011.
Inoue et al., Replication-Dependent Loss of 5-Hydroxymethylcytosine in Mouse Preimplantation Embryos, Science, 334: 194, 2011.
Inoue et al., Generation and replication-dependent dilution of 5fC and 5caC during mouse preimplantation development, Cell Res, 21: 1670-1676, 2011.
Korlach and Turner, Going beyond five bases in DNA sequencing, Curr.Opin.Struct.Biol., 22: 251-261, 2012.
Calmann and Marinus, Regulated Expression of the Escherichia coli dam Gene, J. Bacteriol., 185(16): 5012-5014, 2003.
Song et al., Mapping recently identified nucleotide variants in the genome and transcriptome, Nature Biotechnol, 30 (11): 1107-1116, 2012.
Beck, Taking the measure of the methylome, Nature Biotechnol, 10: 1026-1028, 2010.
Lee et al., Transcriptional Regulatory Networks in Saccharomyces cerevisiae, Science, 298: 799-804, 2002.
Eisen et al.,Cluster analysis and display of genome-wide expression patterns, Proc. Natl. Acad. Sci., 95: 14863-14868, 1998.
Tavazoie et al., Systematic determination of genetic network architecture, Nat. Genet., 22: 281-285, 1999.
Bussemaker et al., Regulatory element detection using correlation with expression, Nat. Genet., 27: 167-171, 2001.
Ding et al., Single-molecule mechanical identification and sequencing, Nature Met, 9(4): 367-372, 2012.
Woodside et al., Nanomechanical measurements of the sequence-dependent folding landscapes of single nucleic acid hairpins, Proc. Natl. Acad. Sci. U.S.A., 103 (16): 6190-6195, 2006.
Carey et al., Confirming the Functional Importance of a Protein—DNA Interaction, Cold Spring Harb Protoc, 2012 (7): 733-57, 2012.
Matys et al., TRANSFAC(R) and its module TRANSCompel(R): transcriptional gene regulation in eukaryotes, Nucleic Acids Res., 34: D108-D110, 2006.
Tadepally et al., Evolution of C2H2-zinc finger genes and subfamilies in mammals: Species-specific duplication and loss of clusters, genes and effector domains, BMC Evol. Biol., 8: 176, 2008.
Guest, C.R. et al., Interaction of DNA with the Klenow Fragment of DNA Polymerase I Studied by Time-Resolved Fluorescence Spectroscopy (1991) Biochemistry30:8759-70.
Heyduk, T., and Lee, J.C., Application of fluorescence energy transfer and polarization to monitor Escherichia coli cAMP receptor protein and lac promoter interaction (1990) Proc. Natl. Acad. Sci. USA. 87:1744-8.
Letilly, V., and Royer, C.A., Fluorescence Anisotropy Assays Implicate Protein-Protein Interactions in Regulating trp Repressor DNA Binding (1993) Biochemistry32:7753-8.
Lundblad J.R. et al., Fluorescence Polarization Analysis of Protein—DNA and Protein-Protein Interactions (1996) Mol. Endocrinol. 10:607-12.
Royer, C.A. et al., Analysis of Binding in Macromolecular Complexes: A Generalized Numerical Approach (1992) Anal. Biochem. 191:287-94.
International Search Report from corresponding PCT/EP2014/051272, dated Mar. 7, 2014.

* cited by examiner

PROCESS FOR DETECTION OF DNA MODIFICATIONS AND PROTEIN BINDING BY A SINGLE MOLECULE MANIPULATION

CROSS REFERENCE TO RELATED APPLICATIONS

This application is a § 371 National Stage Application of PCT/EP2014/051272, filed 22 Jan. 2014, which claims priority to EP 13305074.0, filed 22 Jan. 2013.

BACKGROUND

Field of the Invention

The present invention relates to a method for determining whether a protein binds to a specific DNA sequence. This method is useful in particular for identifying modifications to the DNA sequence (e.g. methylations) via the binding of proteins that specifically recognize those modifications (e.g. antibodies), but also to identify the binding sequence on DNA of a variety of proteins.

Description of Related Art

Protein binding to DNA is a major phenomenon in biology; it has a fundamental role in regulating cellular and viral functions. These include fundamental cellular processes such as DNA replication, transcription, DNA repair, and DNA recombination, but also DNA modification or the maintenance of the chromosome architecture.

There are several proteins that bind to specific sites in the genome to regulate genome expression and maintenance. DNA-binding proteins constitute a large family of proteins with diverse and important biological functions. The family of DNA-binding proteins is one of the most populated and studied amongst the various genomes of bacteria, archea and eukaryotes. Most of these proteins, such as the eukaryotic and prokaryotic transcription factors, contain independently folded units (domains) in order to accomplish their recognition with the contours of DNA. They include important gene-regulatory proteins known as transcription factors and DNA-processing proteins, such as e.g. DNA and RNA polymerases, DNA ligases, DNA helicases, DNA endonucleases and exonucleases, and DNA repair and recombination proteins.

Identifying the sites bound by these proteins has proven to be a daunting task. For example, in the human genome, there are more than 700 predicted $C_2H_2$ zinc-finger transcription factors (Tadepally et al., BMC Evol. Biol., 8: 176, 2008), but only about 10% of these have known binding motifs (Matys et al., Nucleic Acids Res., 34: D108-D110, 2006). Moreover, while the thermodynamical equilibrium properties of the protein binding to DNA are well-known, measuring the kinetics of their binding and unbinding is a more challenging problem.

DNA-protein interactions are studied using a variety of methods such as gel-shift assays, footprinting, and transcriptional activation (Carey et al., Cold Spring Harb Protoc, 2012(7): 733-57, 2012). While each of these methods may contribute distinct information about the location or effect of binding, they do not provide a simple way of quantitatively measuring specific binding. Fluorescence polarization/anisotropy provides a rapid, non-radioactive method for accurately measuring DNA-protein binding directly in solution without using filter binding, electrophoresis, or precipitation steps (Guest et al., 1991; Heyduk and Lee, 1990; LeTilly and Royer, 1993; Lundblad et al., 1996; Royer et al., 1992).

The molecular mechanisms by which genomic information directs the synthesis of different biomolecules has been the focus of much of molecular biology research over the last three decades. Previous studies have typically concentrated on individual genes, with the resulting general principles then providing insights into transcription, chromatin remodeling, messenger RNA splicing, DNA replication and numerous other genomic processes. Although many such principles seem valid as additional genes are investigated, they generally have not provided genome-wide insights about biological function. On the other hand, systematic analyses of transcripts and regulatory information are essential for the identification of genes and regulatory regions, and are an important resource for the study of human biology and disease. Such analyses can also provide comprehensive views of the organization and variability of genes and regulatory information across cellular contexts, species and individuals.

Genome-wide efforts such as the Encode project (Encyclopedia of DNA Elements) to identify e.g. all the transcription-factor-binding sites in the human genome have proven cumbersome and extremely Labor-intensive (The ENCODE Project Consortium, Nature, 489: 57-74, 2012).

There is thus still a need for a simple and reliable method for detecting protein/nucleic acid interactions.

SUMMARY

The present invention relates to a method for the determination of the binding of a protein to a nucleic acid molecule by physical manipulation.

The method according to the present invention, based on physical techniques and electronic treatments, differs from the current approaches, which are chemical or biochemical. It offers numerous advantages over the prior art:
1) It is highly sensitive, since it is based on the detection of a single protein or protein complex molecule to a single nucleic acid molecule. Using single molecule offers the ability to measure not only the time required for a protein to find its nucleic acid target and the time it stays on its target, but also the accurate location of the binding event.
2) It does not use expensive labelled nucleotides (either with fluorophores or some other groups).
3) It enables to determine the precise localization (in bp) of the protein binding site along a double stranded nucleic acid by measuring the distance between the two ends of the said double-stranded nucleic acid molecule.
4) The measurement can be repeated periodically on a second time-scale, thus leading to elimination of false positives, improved statistics and a significant reduction in instrumental drifts.
5) The experiment can be repeated many times on the same molecule, thus improving the statistics and the reliability of the measurement.
6) It enables the detection of any nucleic acid binding protein. Proteins which specifically recognize structural modification of the nucleic acid can thus be identified, leading to the detection of the sites of the structural modification.

The present invention relates to a method for the detection of the binding of a protein to a nucleic acid sequence based on the physical localization on the sequenced nucleic acid molecule of the sites where the protein is bound.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF A PREFERRED EMBODIMENT

Figure 1:
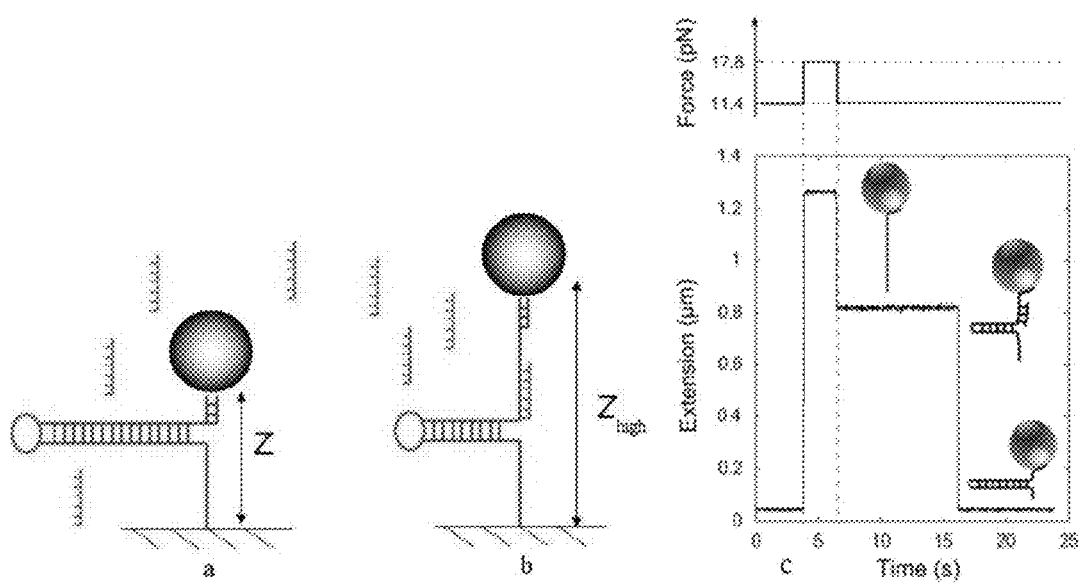
FIGS. 1-13 depict embodiments as described herein.

In the context of the present invention, 'binding' refers to a non-covalent interaction between macromolecules (e.g., between a protein and a nucleic acid). Such interactions are generally characterized by a dissociation constant ($K_d$) of $10^{-6}$ $M^{-1}$ or lower. 'Affinity' refers to the strength of binding: increased binding affinity being correlated with a lower $K_d$.

By 'detection of the binding of a protein to a nucleic acid molecule', it is herein meant all the activities leading directly or indirectly to the obtainment of some information on the presence or absence of an interaction between the said protein and the said nucleic acid molecule. The detection of the said binding may or may not involve the determination of additional information, such as e.g., the kinetic parameters of the binding reaction or the sequence of the site bound by the protein. As will be apparent to the person of skills in the art, the method of the invention allows for such determination to be performed easily.

The invention is based on the observation that the two strands of a denatured double-stranded nucleic acid will re-hybridize under appropriate conditions. If a molecule is bound to any of the strands of the said denatured double-stranded nucleic acid molecule during the re-naturation step, the re-hybridization will only be partial. The inventors have now found that, under certain conditions, this pause in re-hybridization, be it permanent or transient, can be used to detect an interaction between a protein and the said denatured double-stranded nucleic acid molecule. According to the invention, it is possible to detect a blockage of the re-hybridization of the double-stranded nucleic acid molecule; the physical parameters (e.g. the duration of the blockage, the position of the blockage on the double-stranded nucleic acid molecule) associated with this blockage then allow the detection of an interaction between a protein and the sequence of the nucleic acid.

The present invention thus relates to a method for the determination of the binding of a protein to a nucleic acid molecule, said method comprising a step of detecting a blockage of the re-naturation of a denatured double stranded nucleic acid molecule.

By 'denaturation', it is herein meant the process of separation of the two strands of a double-stranded nucleic acid molecule occurring when most of the hydrogen bonds between the said strands are broken. The denaturation process yields a denatured nucleic acid molecule, by which it is herein meant the two separated complementary strands resulting from the denaturation of a double-stranded nucleic acid molecule. By 're-naturation', it is herein referred to the process by which two separated complementary strands reform through hybridization into a double helix. As used herein, 'hybridization' is the process of establishing a non-covalent, sequence-specific interaction between two or more complementary strands of nucleic acids into a single hybrid.

There are several possibilities known to the skilled person to denature the nucleic acid. In a most preferred manner, the two strands are separated by submitting them to a physical force. A 'physical force' according to the invention is any influence that causes an object to undergo a certain change, either concerning its movement, direction, or geometrical construction. It will be clear to the skilled person that a force according to the invention is different from other physical parameters such as e.g. temperature (which is a direct property of matter rather than an influence exerted thereon). Physical forces according to the invention comprise such forces as friction, tension, normal force, air resistance force, applied force, and elastic force. Most preferably, the physical force according to the invention is a tension force. According to this embodiment, the free ends of the said double-stranded nucleic acid may be pulled apart, thus rupturing all the bonds between the paired bases, and opening the double-stranded nucleic acid.

The invention applies to any type of double-stranded nucleic acid. Most often, the double-stranded nucleic acid will be DNA, but it is understood that the invention also applies to single-stranded DNA-single-stranded DNA duplexes, perfectly paired or not perfectly paired, or alternatively to single-stranded DNA-single-stranded RNA duplexes, perfectly paired or not perfectly paired, or alternatively to single-stranded RNA-single-stranded RNA duplexes, perfectly paired or not perfectly paired. Furthermore, the duplex may consist of at least partial re-pairing of two single strands obtained from samples of different origins. Finally, the invention also applies to the secondary structures of a sole single-stranded DNA or of a sole single-stranded RNA.

Thus, the method of the invention relates to a method for the detection of the binding of a protein to a nucleic acid molecule, said method comprising the steps of:
  denaturing a double-stranded nucleic acid molecule by applying a physical force to the said molecule; and
  detecting a blockage of the re-naturation of the double-stranded nucleic acid.

Advantageously, the said method comprises the further step of determining the position of the blockage.

In this type of method for assaying the binding of a protein to a DNA molecule, it can be advantageous, in order to facilitate re-pairing, to arrange for the free ends of the double-stranded DNA molecule (i.e. the ends which are not attached to supports) to be joined to one another covalently or quasi-covalently before pulling apart. In a preferred embodiment, the double-stranded nucleic acid molecule is a hairpin. If it is desired that the double-stranded nucleic acid be represented diagrammatically in the context of the present invention, it is possible to liken it to a "zip fastener", which is opened (or closed): the denaturation of the double-stranded nucleic acid is the unzipping, the re-naturation the re-zipping.

The inventors have observed that, under certain conditions, when a molecule is bound to the denatured double-stranded nucleic acid molecule, re-naturation of the said double-stranded nucleic acid molecule is blocked. The molecule bound can be of any type of molecule with an affinity for a specific sequence on the said denatured double-stranded nucleic acid molecule, e.g. a nucleic acid, a protein or a small molecule.

In a first aspect of the invention, a protein is used to block the re-naturation of the said double-stranded nucleic acid.

The terms 'protein', 'proteins', 'polypeptide', and 'polypeptides', as used herein, are synonyms and refer to polymers of amino acids covalently linked through peptide bonds into a chain. Peptide bonds are formed between the carboxyl group of one amino acid and the amino group of the next amino acid. The terms also apply to amino acid polymers in which one or more amino acids are chemical analogues or modified derivatives of corresponding naturally-occurring amino acids. The terms "amino acids" and "amino acid" refer to all naturally occurring alpha amino acids in both their D and L stereoisomeric forms, and their analogs and derivatives. An analog is defined as a substitution of an atom in the amino acid with a different atom that usually has similar properties. A derivative is defined as an amino acid that has another molecule or atom attached to it. Derivatives would include, for example, acetylation of an amino group, amination of a carboxyl group, or oxidation of the sulfur residues of two cysteine molecules to form cystine.

Proteins can have several functions. A 'binding protein' is a protein which is capable of binding non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form multimers) and/or it can bind to one or more molecules of a different protein or proteins. A binding protein can have more than one type of binding activity. For example, zinc finger proteins have DNA-binding, RNA-binding and protein-binding activity. A 'nucleic acid-binding protein' according to the invention is thus a protein which is capable of interacting with a nucleic acid. A 'single-stranded nucleic acid-binding protein' according to the invention is thus a protein which is capable of interacting with a single-stranded nucleic acid, while a 'double-stranded nucleic acid-binding protein' according to the invention is thus a protein which is capable of interacting with a double-stranded nucleic acid.

According to this embodiment, the method of the invention thus relates to a method for the determination of the binding of a protein to a nucleic acid molecule comprising a nucleic acid sequence, said method comprising the steps of:
  a) denaturing a said double-stranded nucleic acid molecule comprising the said sequence by applying a physical force to the said molecule;
  b) providing the said protein;
  c) re-naturing the said double stranded nucleic acid molecule in the presence of the said protein and
  d) detecting a blockage of the renaturation of the double-stranded nucleic acid.

Advantageously, the said method comprises the further step of determining the position of the blockage.

As it is well known in the field, nucleic acid-binding proteins may be distinguished on whether they are capable of binding single-stranded nucleic acids (ssDNA and ssRNA) or whether they are capable of binding double-stranded nucleic acids (dsDNA, dsRNA, DNA/RNA hybrids, etc.).

In a first embodiment of the method of the invention, the protein which is used to block the renaturation of the denatured double-stranded nucleic acid is a protein which is capable of binding single-stranded nucleic acid.

Nucleic acid-binding proteins with affinity for single-stranded nucleic acid will be capable of interacting with the denatured double-stranded molecule per se, thus leading to a blockage of the renaturation of the double-stranded nucleic acid. The skilled person will realize that the present invention enables the easy and precise determination of the parameters of the binding reaction kinetics, even if the protein does not bind to a specific sequence. Indeed, single-stranded nucleic acid-binding proteins most often do not have affinity for a specific sequence, but rather for nucleic acids in general. For example, helicases are known to bind to ssDNA gaps in order to unwind dsDNA. Bacterial single-stranded DNA-binding proteins, or SSB, bind to single-stranded regions of DNA to prevent premature annealing, to protect the single-stranded DNA from being digested by nucleases, and to remove secondary structure from the DNA. The Rad52 protein, a protein important for DNA double-strand break repair and homologous recombination, binds single-stranded DNA ends, and mediates the DNA-DNA interaction necessary for the annealing of complementary DNA strands.

These single-stranded nucleic acid-binding proteins have a general affinity for nucleic acids, which means in the context of the present invention that the proteins are capable of binding a single-stranded nucleic acid, regardless of the sequence of the said nucleic acid. Such a non sequence-specific nucleic acid-binding protein binds to a plurality of unrelated DNA sequences with a dissociation constant that varies by less than 100-fold, usually less than tenfold, to the different sequences.

On the other hand, some nucleic acid-binding proteins have affinity for nucleic acid molecules containing a specific sequence, i.e. they only recognize and bind to the nucleic acid comprising the said sequence. Not all components of a binding interaction need be sequence-specific (e.g., contacts with phosphate residues in a DNA backbone), as long as the interaction as a whole is sequence-specific. Indeed, while a great number of single-stranded nucleic acid-binding proteins have only a general affinity for nucleic acids, some of these proteins are capable of binding single stranded nucleic acids at specific sequences. A sequence-specific nucleic acid-binding protein thus binds to a specific sequence or family of specific sequences showing a high degree of sequence identity with each other (e.g., at least about 80% sequence identity) with at least 100-fold greater affinity than to unrelated sequences. The dissociation constant of a sequence-specific nucleic acid-binding protein to its specific sequence(s) is usually less than about 100 nM, and may be as low as 10 nM, 1 nM, 1 pM, or 1 fM.

A large number of nucleic acid-binding proteins are not capable of binding single-stranded nucleic acids. These proteins, which possess affinity for double-stranded nucleic acids rather, will not be capable of interacting with the denatured double-stranded molecule per se. These proteins will most likely not trigger a blockage of the renaturation of the double-stranded nucleic acid under these conditions.

Most of these proteins recognize and bind specific double-stranded nucleic acid sequences. For example, double-stranded DNA-binding proteins play an important role in the regulation of the expression of new proteins. These proteins interact with DNA by means of various structural motifs, and can stimulate or repress transcription of messenger RNA, depending on the properties and location of the DNA sequence to which they bind.

In this case, it may be advantageous to provide a single-stranded nucleic acid molecule with the said double-stranded nucleic acid-binding protein, after denaturing the said double stranded molecule. It is indeed well-known in the art that the said single-stranded nucleic acid can hybridize with a complementary sequence on one of the strands of the denatured double-stranded nucleic acid, thus forming a double-stranded nucleic acid hybrid which can be bound by the protein. This single-stranded nucleic acid can be of any length, provided that it is long enough to block the renaturation process. Preferentially, the length of the single stranded nucleic acid will be comprised between 3 and 50 nucleotides; more preferentially, between 3 and 45 nucleotides, between 3 and 40 nucleotides, between 3 and 35 nucleotides, between 3 and 30 nucleotides, between 3 and 25 nucleotides, between 3 and 20 nucleotides, between 3 and 15 and even more preferentially between 3 and 12. The single-stranded nucleic acid of the invention can be in particular a DNA or an RNA molecule, either natural or modified. The said single-stranded nucleic acid may also be made of modified nucleotides, such as locked nucleic acid (LNA), which are nucleotides in which the ribose moiety is modified with an extra bridge connecting the 2' oxygen and 4' carbon, or peptide nucleic acid (PNA), wherein the backbone is composed of repeating N-(2-aminoethyl)-glycine units linked by peptide bonds.

When a single-stranded nucleic acid molecule is thus added to a denatured double-stranded nucleic acid prior to renaturation, a blockage of re-hybridization indicates that the sequence of the single-stranded nucleic acid molecule is complementary to at least part of the sequence of the double-stranded nucleic acid molecule.

The inventors have shown that when a double-stranded nucleic acid-binding protein is present, it is capable of binding the hybrid formed between the denatured double-stranded nucleic acid and the single-stranded nucleic acid molecule. This interaction between the protein and the nucleic acid hybrid leads an alteration of the duration of the blockage. Most of the time, this interaction leads to an increased blockage of the renaturation. For example, a primase will stabilize DNA oligos that would not otherwise have been sufficiently stable to block the hairpin re-hybridization for a time long enough to be detected. Likewise, the binding of a DNA-polymerase to the 3' end of a small oligonucleotide used as a primer increases its stability. Alternatively, the duration of the blockage may also be reduced. Indeed, the present inventors have shown that the binding of some helicases trigger a destabilization of the said hybrid, which is translated in a shorter blockage time.

According to this preferred embodiment, the method of the invention thus comprises the steps of:
a) denaturing a double-stranded nucleic acid molecule comprising a specific sequence by applying a physical force to the said molecule;
b) providing the said protein and a single-stranded nucleic acid molecule corresponding to the said nucleic acid sequence;
c) renaturing the said double stranded nucleic acid molecule in the presence of the said protein and the said single-stranded nucleic acid molecule; and
d) detecting a blockage of the renaturation of the double-stranded nucleic acid.

This embodiment is particularly advantageous because it allows for the determination of the binding of the said protein to the sequence comprised within the double-stranded nucleic acid.

In a typical configuration, the double-stranded nucleic acid molecules may be specifically anchored on two solid substrates (e.g. microscope slide, micropipette, microparticle). One of the ends may be attached directly or indirectly to a surface, while the other end is attached directly or indirectly to a movable surface. In this embodiment, a tension is applied on both ends of the double-stranded nucleic acid when the supports are moved away. When the tension is higher than a threshold value, the two strands are separated and the nucleic acid molecule is denatured. The tension applied is preferentially above or equal to 15 pN; it is more preferentially above or equal to 16 pN; it is even more preferentially above or equal to 17 pN; in a very much preferred aspect, it is above or equal to 18 pN. This force may vary with temperature, nucleotide type and buffer, but the skilled person will easily adapt the said force with regard to these parameters in order to obtain the separation of the two strands. On the other hand, when the tension is decreased under a minimal value, the two strands of the denatured double-stranded nucleic acid can re-hybridize. To obtain re-hybridization of the said two strands, a tension of less than or equal to 12 pN is preferentially applied; more preferentially, it is less than or equal to 11 pN; even more preferentially, it is less than or equal to 10 pN.

Most preferably, the double-stranded nucleic acid is a hairpin. As used herein, 'hairpin' means a double helix wherein the 5' end of one strand is physically linked to the 3' end of the other strand through an unpaired loop. The said physical link can be either covalent or non-covalent. Preferentially, the said physical link is a covalent bond. Thus, a hairpin consists of a double-stranded stem and an unpaired single-stranded loop. In a hairpin, the ends of the two strands which are not engaged in the loop are free and can thus be pulled apart. This results in the unpairing of the double stranded nucleic acid, thus yielding a denatured double stranded nucleic acid molecule. It is possible to open completely a hairpin double-stranded nucleic acid molecule by pulling on each end of the said nucleic acid molecule with a force higher than a threshold value. When the tension applied to the molecule is decreased to Less than a minimal value, the nucleic acid molecule re-hybridizes to reform a hairpin. The presence of a protein bound to the said denatured nucleic acid molecule (e.g. ssDNA) Leads to a pause in re-hybridization. Likewise, the presence of a single-stranded nucleic acid molecule hybridized to one of the nucleic acid strands of the opened hairpin leads to a pause in re-hybridization, the duration of said pause being modified (i.e. either increased or decreased) when a double-stranded nucleic acid-binding protein is bound to the complex. Therefore, the detection of a change in the duration of such a pause indicates that a protein is bound to at least part of the double-stranded stem.

It is advantageous in this respect to design the loop sequence and Length so that the hairpin refolds after a short transient, e.g. 1 second. Methods to this effect have been described in the prior art, e.g. in Woodside et al., *Proc. Natl. Acad. Sci. U.S.A.*, 103 (16): 6190-6195, 2006). When the force is decreased from the opening to the test value, the extension of the open hairpin varies because of the elasticity of single stranded DNA. The small delay before the hairpin refolds allows the user to determine the hairpin extension at the same force than the one used to detect the blocking state.

Using a hairpin makes it possible, in particular, to perform cycles of pairing and unpairing and thus to improve the signal/noise ratio.

Techniques allowing the free ends of double-stranded nucleic acid to be joined together are known, and some will be described in greater details in what follows.

By determination of the blockage, it is herein meant the determination of the physical parameters associated with the blockage. One useful parameter is the position of the blockage on the double-stranded nucleic acid molecule, said position corresponding to the position of binding of the protein to the opened double-stranded nucleic acid molecule or to the hybridization of the single-stranded nucleic acid molecule on the said opened double-stranded nucleic acid molecule. Indeed, the inventors have found that the position on the double-stranded nucleic acid at which the pause in renaturation occurs can be precisely determined: the use of a hairpin affords the skilled person a means to determine the physical distance between the two free ends of the hairpin at any time during the denaturation/renaturation process.

Thus, it is particularly advantageous according to the present invention that the said method comprises a further step of determining the position of the blockage.

According to this preferred embodiment, the invention provides a method for the determination of the binding of a protein to a nucleic acid molecule comprising a nucleic acid sequence, said method comprising the steps of:

a) denaturing a double-stranded nucleic acid molecule comprising a nucleic acid sequence by applying a physical force to the said molecule;
b) providing the said protein;
c) renaturing the said double stranded nucleic acid molecule in the presence of the said protein;
d) detecting a blockage of the renaturation of the double-stranded nucleic acid; and
e) determining the position of the said blockage on the said double-stranded nucleic acid molecule.

By 'free end' it is herein meant the end of one strand which is not covalently inked to an extremity of the other strand; as explained above, these free ends may each be bound to a different surface. For example, one of these surfaces may be movable, whilst the other may be motionless. The skilled person will thus easily realize that, in order to measure the distance between the free ends of the hairpin double-stranded nucleic acid, it is possible to simply measure the distance between the two surfaces.

This distance is maximal ($z_{high}$ ($F_{open}$)) when the hairpin molecule is completely denatured, since the hairpin nucleic acid is then completely extended; it is minimal ($z_{low}$ ($F_{test}$)) when the said hairpin molecule is completely renatured. It is advantageous to perform all length comparisons at the same force $F_{test}$, so that the single stranded nucleic acid has the same elastic properties. Using the delay in loop closing the skilled user can measure $z_{high}$ ($F_{test}$). Likewise, the distance between the two free ends when the renaturation process is temporarily paused can be measured: as expected, this distance z is comprised between $z_{high}$ and $z_{low}$ (all z being measured with F=$F_{test}$). It is immediately clear that the distance z varies with the localization in the hairpin molecule of the binding site of the single-stranded nucleic acid-binding protein, or of the sequence to which the single-stranded nucleic acid is complementary. If the said protein is bound to a sequence which is located close to the free ends of the hairpin, the self-rehybridization process is blocked just before the complete hairpin is reformed; in this case, $z_{pause}$ is minimal. On the other hand, if the said protein binds to a part of the hairpin which is close to the unpaired loop, the renaturation process will be arrested in a situation where the hairpin is completely, or almost completely denatured; in this case, $z_{pause}$ is maximal. Likewise, if the said single-stranded nucleic acid hybridizes with a sequence which is located close to the free ends of the hairpin, the self-rehybridization process is blocked just before the complete hairpin is reformed; in this case, $z_{pause}$ is minimal. On the other hand, if the said single-stranded nucleic acid hybridizes with a part of the hairpin which is close to the unpaired loop, the renaturation process will be arrested in a situation where the hairpin is completely, or almost completely denatured; in this case, $z_{pause}$ is maximal (FIG. 1).

It is possible to correlate precisely a physical distance in a double-stranded nucleic acid molecule with a number of bases. For example, a distance of 0.8 nm corresponds to the distance spanned by two successive nucleotides (1 bp) in a single strand nucleic acid under a 10 pN force. The exact calibration of extension versus force is given by the elasticity of single stranded nucleic acid. Therefore, by simply measuring the distance between the two free ends of the partially re-zipped double-stranded nucleic acid molecule (or any two reference positions on the molecule), it is possible to determine precisely where the renaturation is blocked.

Thus, in one embodiment, the invention consists of a method for the determination of the binding of a protein to a nucleic acid molecule, wherein the said double-stranded nucleic acid molecule is first denatured by application of a physical force, then re-hybridized in a presence of the said protein, and optionally of a single-stranded nucleic acid, and the presence of a blockage in the re-hybridization detected. In one aspect, the distance between the two ends of the partially renatured double-stranded molecule is determined when the renaturation process is blocked. Preferentially, the distance between the two ends of the said molecule is determined when the molecule is completely denatured. More preferentially, the two distances are compared and the position of the blockage is determined. More preferentially, the distance between the fully extended loop and a reference hybridization position is measured and used to determine the position of the blockage. Even more preferentially the distance between two reference hybridization positions is measured and used to determine the position of the blockage.

Aside from its position along the molecule, the most useful parameter associated with the blockage in renaturation is the period of time during which the renaturation is blocked (referred herein as the duration of the pause in renaturation). Indeed, it is possible to measure the period of time during which the rehybridization is blocked. For example, the skilled person can determine the period of time during which the distance between the two ends of the double-stranded nucleic acid is z as defined above, i.e. an intermediate value comprised between $z_{high}$ and $z_{low}$.

When the blockage is caused by the hybridization between the denatured double-stranded nucleic acid and the complementary single-stranded nucleic acid, the duration of the blockage is dependent upon the degree of complementarity between the two sequences. The higher the complementarity, the greater the number of bonds established between the two molecules, and therefore the longer the duration. It is also clear that the blockage time will be dependent upon the length of the region of complementarity between the two sequences. The longer the region, the greater the number of bonds established between the two molecules, and therefore the longer the duration. It is therefore easily conceivable that under certain conditions the duration of the renaturation pause will be almost permanent. In particular, when the single-stranded nucleic acid comprises more than 20, preferably more than 25, even more preferably more than 30 nucleotides capable of hybridizing with the denatured double-stranded nucleic acid, the single-stranded nucleic acid remains hybridized to the double-stranded hairpin (for many minutes) even when the force applied to the said double-stranded nucleic acid is decreased to $F_{test}$, thus preventing self-re-hybridization of the said double-stranded hairpin. In such a case, it may be advantageous to use an enzyme to eject the single-stranded nucleic acid molecule or to add a third phase where the force is reduced to 0.5 or 1 pN for a few seconds which efficiently expels hybridized oligonucleotides. The ejection of the said single-stranded nucleic acid molecule thus makes it possible to perform cycles of pairing and unpairing and thus improve the signal/noise ratio.

The duration of the pause may also vary with the conditions of the reaction. Said duration will decrease as the temperature increases. Likewise, the buffer conditions can also modulate the duration of the pause: for example, magnesium, betain and tetramethylammonium chloride (TMAC used at molar concentration) increase the blocking time. These compounds reinforce AT pairs more than GC, thus reducing the difference in strength between these pairs. However, when the temperature and the buffer are fixed, the duration of the pause will only depend on the force pulling on the denatured double-stranded nucleic acid and on its complementarity with the single-stranded nucleic acid. In fact, the inventors have shown that the blockage time decreases exponentially as the force is reduced.

Finally, the duration of the pause will also be dependent upon the properties of the complex formed between the protein, the denatured double-stranded nucleic acid and the complementary single-stranded nucleic acid. The presence of the double-stranded acid nucleic-binding protein may stabilize the complex. The higher its affinity for double-stranded nucleic acid, the longer the pause appears. It is also possible that the protein destabilizes the double-stranded nucleic acid (as is the case for e.g. the open-complex of an RNA-polymerase), leading to a shorter pause.

Likewise, the presence of a protein capable of binding the denatured double-stranded nucleic acid will block transiently the renaturation of the said nucleic acid molecule. The duration of this blockage will also be dependent upon the affinity of the protein for the nucleic acid. It is clear that a protein with a high affinity for the said molecule will lead to a longer pause than a protein with a weaker affinity.

The skilled person will immediately realize that the measurement of the pause enables the determination of the mean time of blockage and hence the kinetics parameters of the binding reaction, as explained in the experimental section.

Thus, in one particular aspect, the method of the invention comprises the steps of:
a) denaturing the said double-stranded nucleic acid molecule by applying a physical force to the said molecule;
b) providing a protein and, optionally, a single-stranded nucleic acid molecule,
c) renaturing the double-stranded nucleic acid molecule in the presence of the said protein and, optionally, of the said single-stranded nucleic acid molecule; and
d) detecting a blockage of the renaturation of the said double-stranded nucleic acid molecule, and
e) determining the duration of the pause.

Preferably, the said method comprises the further step of determining the position of the blockage.

In this embodiment, the duration of the pause may be compared to a control. In particular, when the said protein is a double-stranded nucleic acid-binding protein, it may be advantageous to compare the said pause to a pause measured when the method is performed in the absence of the protein. As explained above, the binding of the protein to the complex formed between the denatured double-stranded nucleic acid and the complementary single-stranded nucleic acid alters the duration of blockage of the renaturation. Said blockage translates as an increase, or decrease (depending on the specific protein) in the duration of the pause.

Thus, in one preferred embodiment, the method of the invention comprises the steps of:
a) denaturing the said double-stranded nucleic acid molecule by applying a physical force to the said molecule;
b) providing a protein and, optionally, a single-stranded nucleic acid molecule,
c) renaturing the double-stranded nucleic acid molecule in the presence of the said protein and, optionally, of the said single-stranded nucleic acid molecule; and
d) detecting a blockage of the renaturation of the said double-stranded nucleic acid molecule, and
e) determining the duration of the pause; and
f) comparing with the duration in absence of protein.

Advantageously, the said method comprises the further step of determining the position of the blockage.

Although it is possible to detect and measure the binding of the protein to a nucleic acid without seeking information on the binding site sequence, it may be useful in some applications to determine the said sequence. For example, it may be interesting to identify mutations of the said binding site which abolish the binding of the said protein.

Thus, in one preferred embodiment, the method of the invention thus relates to a method for the determination of the binding of a protein to a double-stranded nucleic acid molecule comprising a nucleic acid sequence, said method comprising the steps of:
a) denaturing the said double-stranded nucleic acid molecule by applying a physical force to the said molecule;
b) providing the said protein and optionally a single-stranded nucleic molecule complementary to at least part of the said double-stranded nucleic acid molecule;
c) renaturing the said double stranded nucleic acid molecule in the presence of the said protein and optionally the said single-stranded nucleic acid;
d) detecting a blockage of the renaturation of the double-stranded nucleic acid; and
e) sequencing the nucleic acid sequence bound by the said protein.

Advantageously, the detection of the blockage of the renaturation is followed by a step of determining the position of the blockage.

Preferably, the said protein and the said single-stranded nucleic acid molecule are washed off the double-stranded nucleic acid molecule before the binding site is sequenced.

Since the method of the invention is based on the detection of a single molecule, it would be convenient to use a method which can sequence a single molecule without prior amplification. Such single-molecule identification and sequencing methods have been previously described (WO 2011/147931; WO2011/147929; Ding et al., *Nature Met*, 9(4): 367-372, 2012). These sequencing methods are based on the detection of a blockage of the renaturation of a denatured double-stranded nucleic acid molecule. Thus, a sequencing method according to the invention preferably comprises the steps of:
a) denaturing a double-stranded nucleic acid molecule corresponding to the said nucleic acid sequence by applying a physical force to the said molecule;
b) providing a single-stranded nucleic acid molecule;
c) renaturing the said double stranded nucleic acid molecule in the presence of the said single-stranded nucleic acid molecule; and
d) detecting a blockage of the renaturation of the double-stranded nucleic acid.

Advantageously, the said method comprises the further step of determining the position of the blockage.

These sequencing methods can be easily combined with the method of the invention, since they use the same apparatus as the present method. By pulling on magnetic beads tethered by a hairpin to the surface, the molecule can be unzipped. In this open state it can hybridize with complementary single-stranded nucleic acids, which transiently block the hairpin rezipping when the pulling force is reduced. By measuring the distance from the surface to the bead of a blocked hairpin, one can determine the position of the hybrid along the molecule with nearly single-base precision, hence establishing what the local sequence is (the complement of the sequence of the known single stranded nucleic acids in solution). It is thus possible to sequence directly the molecule bound by the said protein, without altering the setup of the experiment, by just replacing the buffer containing the protein and optionally a complementary single-stranded nucleic acid, by a buffer suitable for sequencing according to the said methods.

Efficient identification of DNA cis-regulatory elements is a central challenge of post-genome biology. Identification of all the binding sites of a specific nucleic acid-binding protein in the genome is particularly useful, since it identifies all the genes whose expression is potentially regulated by the said protein. Comprehensive identification of DNA cis-regulatory elements is crucial for a predictive understanding of transcriptional network dynamics.

The confluence of whole genome DNA sequence data, high-throughput technologies, and novel algorithms is rapidly advancing our ability to identify and characterize transcriptional regulatory elements (Eisen et al., *Proc. Natl. Acad. Sci.*, 95: 14863-14868, 1998; Tavazoie et al., *Nat. Genet.*, 22: 281-285, 1999; Bussemaker et al., *Nat. Genet.*, 27: 167-171, 2001; Lee et al., *Science*, 298: 799-804, 2002). However, these approaches have inherent imitations. For example, the success of hybrid methods which use gene expression clustering and cis-regulatory motif discovery is Limited by the range of physiological perturbations used in the Laboratory. The same is true for in vivo approaches such as chip-based chromatin immunoprecipitation (ChIP), where DNA-protein interactions, by the very virtue of their regulatory role, only occur under specific environmental conditions (Lee et al., *Science*, 298: 799-804, 2002). These limitations are even more severe for metazoan eukaryotes, where the experimental data are more difficult to acquire.

The present method offers an alternative to the methods of the prior art, such as ChIP (chromosome immunoprecipitation) and DNAse I footprinting to map the binding locations in the genome of transcription factors (The ENCODE Project Consortium, *Nature*, 489: 57-74, 2012).

Thus according to another aspect, the invention also relates to a method for identifying nucleic acid molecules comprising a sequence capable of binding a specific nucleic acid-binding protein, said method comprising the steps of:
   a) providing a population of double-stranded nucleic acid molecules;
   b) testing the binding of the said protein to the said nucleic acid molecule by the method described above; and
   c) selecting the nucleic acid molecules capable of binding the said protein.

Preferably, the method involves the provision of a single-stranded nucleic acid complementary of the binding site of the said nucleic-acid molecule.

According to this embodiment, the method thus comprises the steps of:

a) providing a population of double-stranded nucleic acid molecules;
   b) denaturing the said double-stranded nucleic acid molecule by applying a physical force to the said molecule;
   c) providing the said protein and a single-stranded nucleic acid molecule complementary to the said binding site;
   d) renaturing the said double stranded nucleic acid molecule in the presence of the said protein and the said single-stranded nucleic acid molecule; and
   e) detecting or not a blockage of the renaturation of the double-stranded nucleic acid; and
   f) selecting the nucleic acid molecules where renaturation is transiently or permanently blocked.

Advantageously, the said method comprises the further step of determining the position of the blockage.

The nucleic acid molecules to be thus isolated correspond to a population of nucleic acid molecules, which comprise the said specific binding sequence. They thus differ from other nucleic acid molecules in that they contain this specific sequence. Although these molecules all share this sequence, they may or may not be identical otherwise. In certain embodiments, it may be preferable for the skilled person to identify the sequence of each nucleic acid molecules which differs outside the said specific binding sequence. Indeed, when identifying nucleic acid molecules containing one or more binding sites for a specific nucleic acid-binding protein, it may be advantageous to sequence the molecules identified, for example with the sequencing method described above. The information obtained by this step may enable the localization of the said molecule on the whole genome and thus identify the expression units which may or may not be regulated by this binding site. This may be achieved easily by carefully using the information obtained by the sequencing step to search the databases: the person of skills in the art knows how to look for clones containing the sequences obtained by sequencing, with the help of publicly-available sequence databases (e.g. Genbank) and this needs not be further detailed here.

In a preferred embodiment, the population of double-stranded nucleic acid molecules represents the whole genome.

The population of double-stranded nucleic acid molecules is advantageously obtained by digesting first the chromosomes by a rare-cutter restriction enzyme. As known by the person of skills in the art, a rare-cutter restriction enzyme is a restriction enzyme with a recognition sequence which occurs only rarely in a genome, for example a recognition sequence comprising 7 or 8 bases. Examples of such rare-cutter enzymes include Sfil, Xma I, Asc I, AsiS I (isoschizomer Sgf I), Not I (isoschizomer CciN I), Sbf I (isoschizomers Sse8387 I, Sda I), Fse I, Pac I etc. ALL these enzymes are commercially available. In a second step, the restriction fragments thus obtained are digested with a common, 6-base restriction enzyme, such as EcoRI, BamHI, XhoI, etc. The resulting linear double-stranded fragments can then be transformed into hairpins. Techniques allowing the free ends of double-stranded to be joined together are known and some are described in greater details in what follows.

Another particular application of the method of the invention is in the detection of epigenetic modifications. Such tests are currently very difficult to conduct and miss many DNA modifications. Yet epigenetic modifications are extremely important in a variety of pathologies including microbial infection and oncology. Advantageously, the aforementioned invention can be used to screen for modifications on genomic DNA either whole or in selected regions.

Epigenetic modifications to DNA are present in the genomes of almost every living organism. Their type and location vary across organisms, tissues, and cell-types; over time; and through interaction with the environment. Some on these modifications come about through carefully controlled cellular processes. Others are the result of DNA damage.

Such modifications greatly expand the quantity of information that can be stored within DNA. For example, the dam gene of *Escherichia coli* encodes a DNA methyltransferase that methylates adenine in -GATC- sequences in double-stranded DNA thus regulating gene expression (see e.g. Calmann and Marinus, *J. Bacteriol.*, 185(16): 5012-5014, 2003). On the other hand, the most common epigenetic marker in eukaryotes is 5-methylcytosine (5mC). This specific modification is required to control and regulate a wide variety of important cellular and broader physiological processes and problems with DNA methylation in humans have been implicated in a variety of diseases, most notably certain types of cancer. In addition to 5mC, a wide variety of other DNA modifications exist in eukaryotes (Korlach and Turner, *Curr. Opin. Struct. Bioi.*, 22: 251-261, 2012).

As of today, the gold-standard for 5mC determination is 'bisulfite conversion' where all cytosine residues are converted into uracil, except those which have been methylated which remain unchanged. Subsequent amplification of the DNA product converts uracil into thymine. These conversion changes can then be detected through sequencing of the DNA (Song et al., *Nature Biotechnol*, 30(11): 1107-1116, 2012). However, this is a complicated, time consuming, and expensive process with error rates of 5-34% (Beck, *Nature Biotechnol*, 10: 1026-1028, 2010).

The present invention provides an easy method for detecting epigenetic modifications of nucleic acids. By 'epigenetic modifications', it is herein referred to modifications of the bases constituting a nucleic acid molecule which take place after the synthesis of said nucleic acid molecule. Such epigenetic modifications include, inter alia, 4-methylcytosine (m4C), 5-methylcytosine (5mC), 5-hydroxymethylcytosine (5hmC), 5-formylcytosine (5fC) and 5-carboxylcytosine (5caC), as well as 6-methyladenosine (m6A) in DNA, and 5-hydroxymethyluracil (5hmU) and $N^6$-methyladenosine (m6A) in RNA.

Thus, in one particular aspect, the present invention provides a method for detecting at least one modified base comprised within a double-stranded nucleic acid molecule, said method comprising the steps of:
  a) providing the said double-stranded nucleic acid;
  b) providing a protein capable of binding said modified base; and
  c) testing the binding of the said protein to the said nucleic acid molecule by the method described above.

Optionally, the method of the invention may comprise a further step of testing the hybridization of a simple oligonucleotide recognizing the site of possible modification to better validate the results. For instance, after detecting the 5mC methylation with its antibody, one can detect the sequence ATGC with a oligo NNTACGNN.

This method is particularly advantageous, because it uses unmodified binding molecules in a reversible process. For instance, when used to detect 5mC, no chemical (sodium bisulfate) reaction on the DNA is required. Moreover, the method of the invention is much more sensitive than any of the methods of the prior art, since it allows for detection of a modified base on a single-molecule basis.

In a preferred embodiment, the modified base is selected in the group constituted by 5-methylcytosine (5mC), 5-hydroxymethylcytosine (5hmC), 5-formylcytosine (5fC) 5-carboxylcytosine (5caC), 5-hydroxymethyluracil (5hmU), and N6-methyladenosine (m6A). In a more preferred embodiment, the said base is chosen between 5mC and 5hmC. In an even more preferred embodiment, the said base is 5mC. Proteins recognizing and binding specifically to these modified bases have been described. For example, antibodies directed against 5mC have been described and used by staining this modification for cell-based visualization (Ito et al., *Nature*, 466: 1129-1133, 2010; Ko et al., *Nature*, 468: 839-843, 2010; Szulwach et al., *Nature Neurosci*, 14: 1607-1611, 2011; Haffner et al., *Oncotarget*, 2: 627-637, 2011; Inoue et al., *Science*, 334: 194, 2011; Inoue et al., *Cell Res*, 21: 1670-1676, 2011). Such antibodies are commercially available (e.g. clone 33D3; ref: 39649 of Active Motif). Besides antibodies, enzymes that specifically recognize and react with the nucleotide of interest have been identified (Song et al., *Nature Biotechnol*, 30(11): 1107-1116, 2012). For example, the T4 bacteriophage enzyme β-glucosyltransferase (βGT) transfers a glucose moiety onto 5hmC. The Tet1-3 proteins are responsible for the conversion of 5mC into 5hmC. Methyl-CpG-binding protein 2, (MeCP2), was first identified by its affinity for DNA containing 5-mC. Preferably, the said protein is an antibody directed against the said modified base or an enzyme specifically recognizing the said base. More preferably, the said protein is an antibody.

It is clear that the same method could be applied to the detection of other modifications of nucleic acids. For example, it is possible to detect a mismatch present in double-stranded nucleic acid molecule. Proteins such as the bacterial MutS have been known for a very long time to recognize the mismatched base on the daughter strand and bind to the mutated DNA. Such property can be put to use to detect and identify any mismatch in a double-stranded nucleic acid molecule.

Therefore, it is also an aspect of the present invention to provide a method for detecting at least one mismatch in a double-stranded nucleic acid, said method comprising the steps of:
  a) providing the said double-stranded nucleic acid;
  b) providing a protein capable of binding a mismatched base; and
  c) testing the binding of the said protein to the said nucleic acid molecule by the method described above.

Since MutS is known to bind as a dimer to a mismatch, it is advantageous to use a MutS dimer in the method of the invention. In eukaryotes, MutS homologs form two major heterodimers: Msh2/Msh6 (MutSα) and Msh2/Msh3 (MutSβ). Preferably, the said protein is selected between a MutS dimer, Msh2/Msh6 (MutSα), and Msh2/Msh3 (MutSβ).

A single-nucleotide polymorphism (SNP, pronounced snip; plural snips) is a DNA sequence variation occurring when a single nucleotide—A, T, C or G—in the genome (or other shared sequence) differs between members of a biological species or paired chromosomes in a human. On average, SNPs occur in the human population more than 1 percent of the time. Because only about 3 to 5 percent of a person's DNA sequence codes for the production of proteins, most SNPs are found outside of coding sequences.

SNPs found within a coding sequence are of particular interest because they are more likely to alter the biological function of a protein.

A molecule comprising a SNP will form a mismatch when hybridized with a molecule comprising the sequence found in the majority of the population. The present invention thus enables the easy detection of SNPs.

This embodiment thus relates to a method for detecting a SNP in a sequence contained in a nucleic acid, said method comprising the steps of:
 a) hybridizing the said nucleic acid with a single-stranded nucleic acid comprising the sequence found in the majority of the population; and
 b) detecting the resulting mismatch by the above method.

If the nucleic acid to be tested is a double-stranded nucleic acid, it may be advantageous to denature the said nucleic acid, before step a).

It is clear that these methods can be performed on a whole-genome scale, by a simple adaptation of the method described above. This will lead to the identification of all the sites in the genome containing e.g. a particular modified base. Genes whose expression is susceptible to be affected by the said modified bases can be identified, by sequencing the nucleic acid molecules containing such modified bases. Moreover, the transmission of the said modified bases to the progeny can then be assessed. These information can be of interest in fields like animal or plant selection, where it is important to ensure that some genes stay silent while others remain expressed throughout the generations.

In yet another aspect, a method is provided for identifying compounds which interfere with the binding of a protein to its specific biding sequence. These compounds diminish or abolish the binding of the said protein to its binding site. Such compounds may be useful as therapeutics. For example, compounds preventing the interaction of the oncogenic forms of cMyc with its binding site would be useful for treating cancer.

According to this embodiment, the invention relates to a method for identifying at least one compound capable of preventing the interaction between a protein and its binding site, said method comprising the steps of:
 a) providing the said protein and a nucleic acid molecule comprising a sequence corresponding to the said binding site;
 b) providing a compound; and
 c) testing the binding of the said protein to the said nucleic acid molecule by the method described above.

In a preferred embodiment, a compound is selected when the binding of the said protein to the said nucleic acid molecule is diminished or abolished.

It is clear that most nucleic-acid binding proteins which are involved in cancer are transcription factors which bind double stranded nucleic acids. Therefore, in another preferred embodiment, the said nucleic acid molecule is a double-stranded nucleic acid molecule. In a further preferred embodiment, the method further comprises providing a single-stranded nucleic acid complementary to the sequence of the said double-stranded nucleic acid molecule. Of course, these molecules are provided before the testing of the binding takes place.

Implementation of the method of the invention has been made possible, in particular, by the existence of devices designed for probing real-time nucleic acid interaction at the single-molecule level. Such a device is described for example in U.S. Pat. Nos. 7,052,650 and 7,244,391. The apparatus described therein uses magnetic traps to apply a picoNewton scale force on a micron-sized superparamagnetic bead. Briefly, the said apparatus comprises an optical microscope, magnets and a PC. The double-stranded nucleic acid molecules are anchored at multiple points at one end to a motionless element, e.g. a surface, and at the other end to a movable surface, in this case a magnetic bead. Magnets are provided for acting on the bead. In particular, the magnets may be used for pulling the bead away from the surface. However, the implementation of the method of the invention is not restricted to the above apparatus. Any device which allows one to fully extend and then refold a molecule of double stranded nucleic acid, whilst monitoring at the same time the extension of the said molecule can be used to implement the method of the invention. For example, optical tweezers may be used; they require however prior force calibration and are not easily parallelized for high throughput measurements. Further drawbacks are the complexity of adjusting torsional control of the nucleic acid and the possible local heating of the solution by the focussed laser which may alter the hybridization conditions.

The double stranded nucleic acid is incubated for a few minutes in a solution of adequate beads (for example streptavidin coated ones) to which it binds by one of its labeled (for example biotin) ends. The beads can be transparent if optical tweezers are later used for manipulation or magnetic if one uses magnetic traps or tweezers for manipulation.

The bead-nucleic acid assembly is injected in a fluidic chamber the surface of which has been treated such as to bind the other labeled end of the molecule (for example a surface coated with anti-Dig to bind the Dig-labeled end of the nucleic acid). The beads are thus anchored to the surface via a nucleic acid hairpin, see FIG. 1a. The distance of the bead to the surface is then monitored by various means known to the man of the art: for example the diffraction rings of their image on a camera can be used to deduce their distance, or the light intensity they scatter (or emit by fluorescence) when illuminated in an evanescent mode can be used to measure their distance. Alternatively, the magnetic field they generate can be measured (using a magnetic sensor such as GMR or Hall sensors) to deduce their distance to a sensor on the anchoring surface.

To pull on the nucleic acid molecule anchoring the beads to the surface various techniques have been described. One can use the light of a focused laser beam to trap a transparent bead near the focal point. By the relative translation of the beam with respect to the anchoring surface one can apply a force on the tethering molecule (a typical optical tweezers assay). The exerted force being proportional to the displacement of the bead from its equilibrium position, to exert a constant force on the tethering molecule requires a feedback loop on the trapping beam.

To exert a constant force on a bead, the use of the hydrodynamic drag generated by a flow around the bead has been described, but it usually yields a low spatial accuracy (>100 nm). The preferred embodiment uses a magnetic trap to pull on super-paramagnetic beads anchored to a surface by a nucleic acid hairpin as described above. In this configuration, small magnets placed above the sample are used to apply a constant force on the anchored bead, whose position can be determined with <1 nm accuracy (depending on the pulling force and the dissipation due to hydrodynamic drag)

In every case one notices that the tethering hairpin can be mechanically fully unzipped by pulling on the beads with a force larger than about 16 pN. Reducing the tension on the molecule to below about 11 pN allows the hairpin to re-zip spontaneously (the unzipping transition is reversible though hysteretic). If, during the unzipped phase, some molecules in solution (such as proteins or complementary oligonucleotides of DNA, RNA, LNA or PNA) have bound to the stretched single stranded nucleic acid, these molecules will block the rezipping of the hairpin when the force is lowered to below 11 pN. The principle of the assay is thus to switch between two forces: a large one $F_{open}$ to open the hairpin and a smaller one $F_{test}$ used to allow re-zipping and to measure the extension of the molecule at transient blockages. The blocking position is related to the sequence by a linear relation between full extension and the blocked one. For best accuracy, the full extension is preferably measured at the test force $F_{test}$. This is achieved by designing the hairpin loop such that it requires a fraction of a second to refold once the force is reduced from $F_{open}$ to $F_{test}$.

In order to attach nucleic acids to surfaces or supports, use may be made of any one of the techniques known in the field. Essentially, the nucleic acid becomes anchored directly to the support, for example the micro-bead, which involves a functionalization of this surface, for example by coating it with streptavidin, a COOH group, and the like, capable of reacting with the functionalized end of the nucleic acid.

Such methods necessitate, in general, functionalizing the nucleic acid, especially the 3' and 5' ends, that is to say grafting appropriate chemical groups onto them. It is, moreover, preferable to join the other two free ends of the molecule by a loop in order to prevent the strands from dissociating at the end of the operation, so that the latter can be repeated if appropriate. For this purpose, different procedures may be adopted.

The simplest is to functionalize, using synthetic oligonucleotides, one of the ends of a double-stranded nucleic acid with two different functions (biotin and amine, for example), which permit anchoring to two different pretreated surfaces. The two strands at the other end may be joined using a partially paired synthetic nucleotide in the form of a loop. In this way, a paired, single-stranded nucleic acid, i.e. a hairpin, is produced from a double-stranded nucleic acid. The advantage of this method lies in its capacity to functionalize a heterogeneous population of large nucleic acid fragments (as are obtained by fractionation of a gene or chromosome), which can then be analyzed simultaneously. In this case, the nucleic acid sample is fractionated using two (or more) restriction enzymes, which enables a subpopulation to be obtained with two different restriction sites at its ends which are similar over all the fragments. This enables the two ends to be treated differently (for example by joining one end to an oligonucleotide in the form of a loop possessing the appropriate restriction site at its end). The drawback of this method lies in the steric interference between the two adjacent functional groups, which can make coupling to the surfaces difficult. To solve this problem, it can be advantageous to add at each free end of the hairpin molecule a "spacer" sequence of bases, to the end of which a functional group is then added; the two spacer sequences are non-complementary, affording each functional group enough space to bind to its dedicated surface. More advantageously, the sequence of each spacer sequence is designed in order to use single-stranded sequencing primers of known sequence in the sequencing method of the invention.

The addition of a loop and/or spacers to the double-stranded nucleic acid molecules can be performed with any of the methods commonly used in molecular biology. These methods are well known to the person skilled in the art and there is thus no need to detail them here.

As regards the actual anchoring techniques, there are many of these and they derive from the techniques for anchoring macromolecules (proteins, DNA, and the like) to commercially available pretreated surfaces. Most of these techniques have been developed for immunology tests, and link proteins (immunoglobulins) to surfaces carrying groups (—COOH, —NH$_2$, —OH, and the like) capable of reacting with the carboxyl (—COOH) or amine (—NH$_2$) ends of proteins.

The covalent anchoring of nucleic acid may be accomplished directly, via the free phosphate of the 5' end of the molecule, which reacts with a secondary amine (Covalink —NH surface marketed by Polylabo at Strasbourg) to form a covalent bond. It is also possible to functionalize DNA with an amine group and then to proceed as with a protein.

There are also surfaces coated with streptavidin (Dynal beads, and the like), which permit quasi-covalent anchoring between the streptavidin and a biotinylated DNA molecule. Lastly, by grafting an antibody directed against digoxigenin onto a surface (by the methods mentioned above), a nucleic acid functionalized with digoxigenin may be anchored thereto. This represents merely a sample of the many possible anchoring techniques.

Among the attachment and anchoring techniques, there should also be mentioned, for example, the techniques described in Patent EP 152 886 using an enzymatic coupling for the attachment of DNA to a solid support such as cellulose.

Patent EP 146 815 also describes various methods of attachment of DNA to a support.

Similarly, patent application WO 92/16659 proposes a method using a polymer to attach DNA.

Naturally, the nucleic acid may be attached directly to the support but, where necessary, especially with a view to imiting the influence of the surfaces, the nucleic acid may be attached at the end of an inert arm of peptide or other nature, as is, for example, described in Patent EP 329 198.

The examples below will enable other features and advantages of the present invention to be brought out.

FIG. 1. Principle of detection of the hybridization of an oligo-nucleotide to its complementary sequence on a hairpin DNA. The hairpin DNA anchoring the bead to the surface (a) is momentarily unzipped by increasing the force pulling on the bead to a value above 16 pN. In that phase the complementary fragment in solution hybridizes to its target on the opened DNA hairpin, thus transiently preventing the re-zipping of the hairpin (b) when the force is reduced back to its initial value. From the change in extension of the molecule ($z_{high}$-z) between the blockage point and the hairpin initial length, one deduces where along the hairpin the complementary sequence has paired. From the average timespan of the blockage one can learn about the possible existence of mismatches and their position along the hybrid. (c) time trace of the extension of a hairpin as the force is increased from 11.4 pN to 17.8 pN and then decreased back to its initial value. One notices the presence of a pause during re-hybridization of about 10 s. That pause is only observed in presence in solution of complementary (or almost complementary) oligomers of length >7 nucleotides (here the signal is due to a 10 mers).

Figure 2:
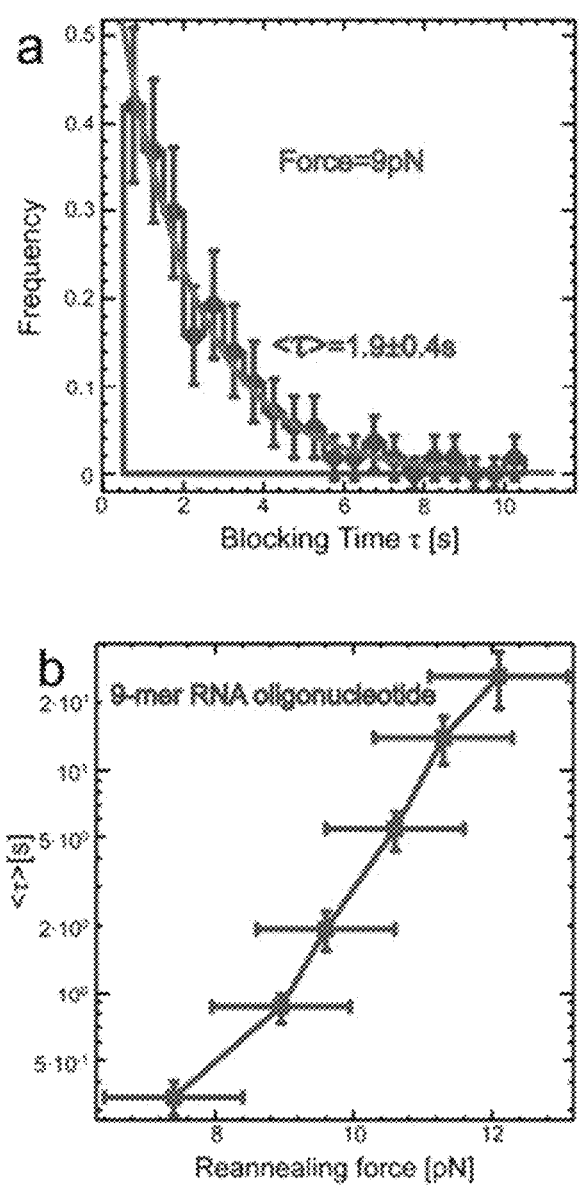

FIG. 2: a) Exponential distribution of the blocking time of a 10 nts oligonucleotide obtained at $F_{test}$=9pN. b) Exponential dependence of $T_{off}$ versus $F_{test}$ obtained for a 9 nts oligonucleotide.

Figure 3:
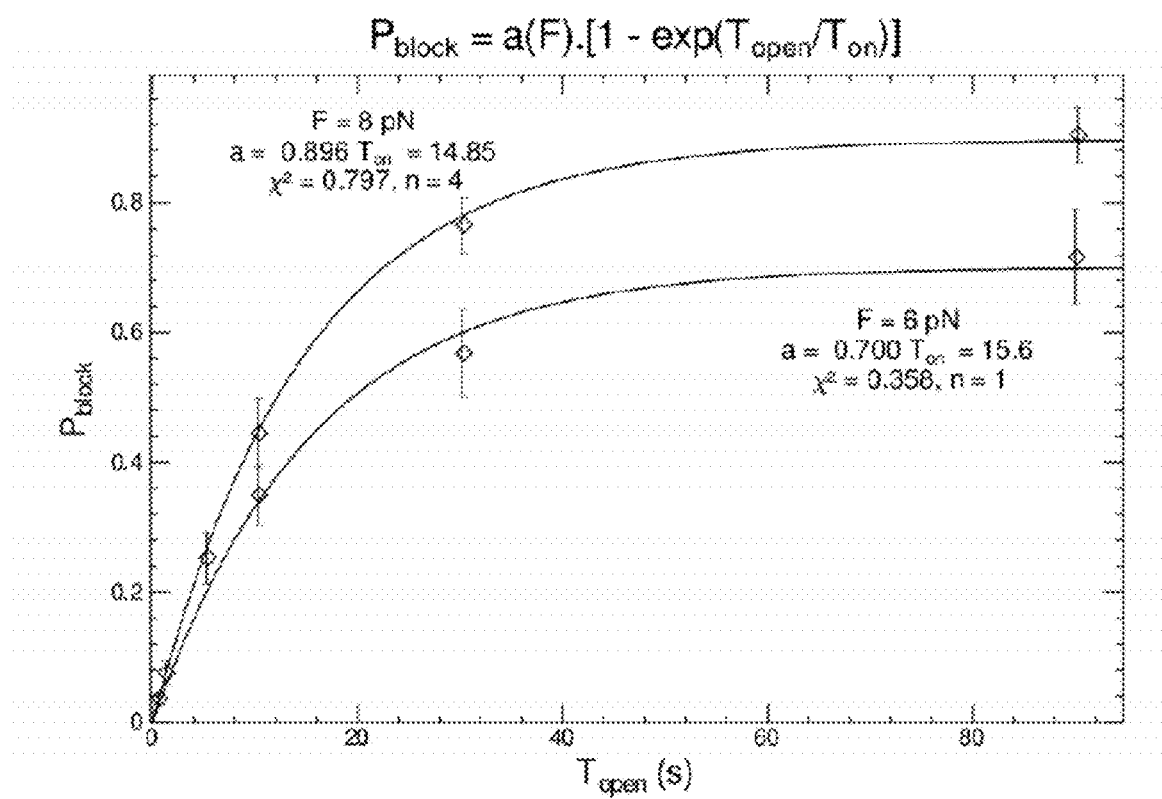

FIG. 3: Evolution of the blocking probability $P_{block}$=Nb.cycles blocked/Nb. Cycles with the duration of the open phase $T_{open}$ for a by a 12-nt oligonucleotide to find its complementary site. A fit demonstrates that Ton the time required for the molecule to find its target is typically 15 s when the oligonucleotide concentration is 20 nM. This time does not depend on the force used in the test phase. The parameter a(F) would be equals to 1 if all events were detected, but since short events are missed a(F) is smaller than 1 especially when $F_{test}$ is small.

Figure 4:
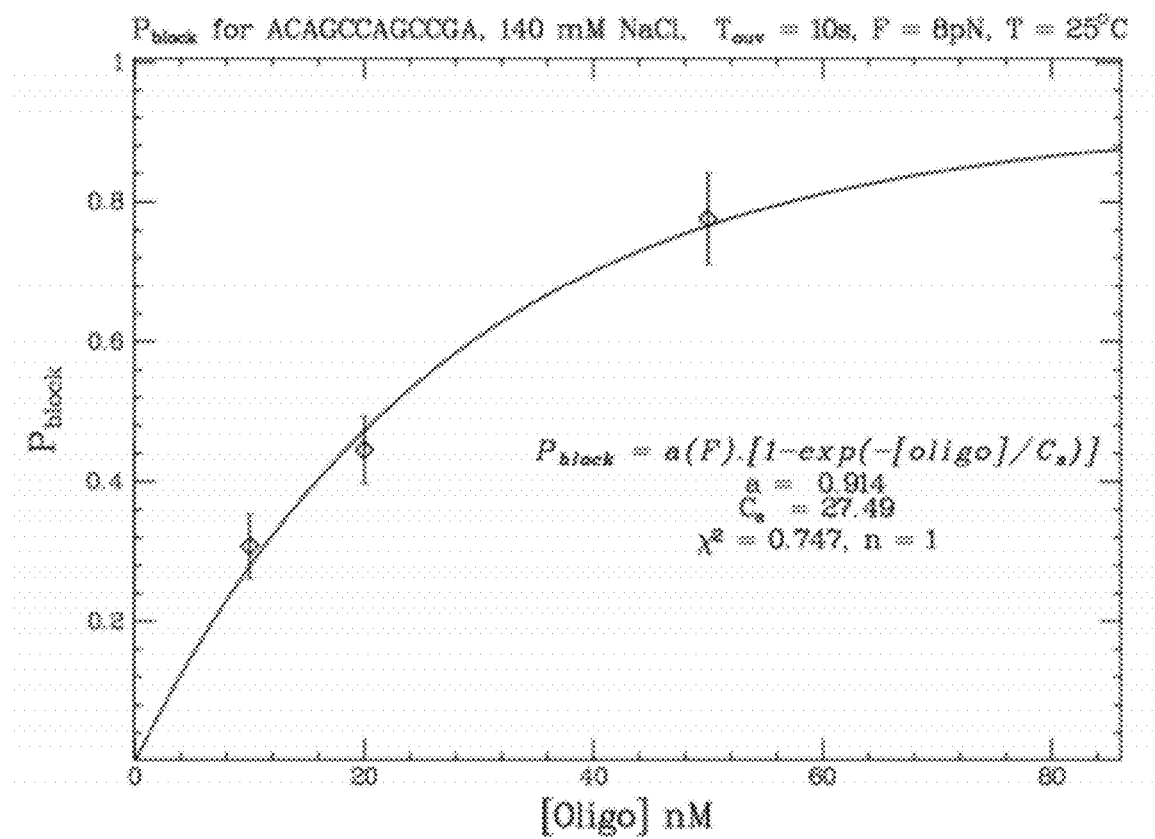

FIG. 4: The blocking probability increases and saturates with the oligonucleotide concentration. Here a 12 nt-oligonucleotide at a concentration of 27.5 nM Leads to a blockage occurring once every two cycles for an open phase lasting 10 s and $F_{test}$=8 pN. As seen in FIG. 3, the saturation of $P_{block}$ does not quite reach 1; this is because we are missing very short blockages.

Figure 5:
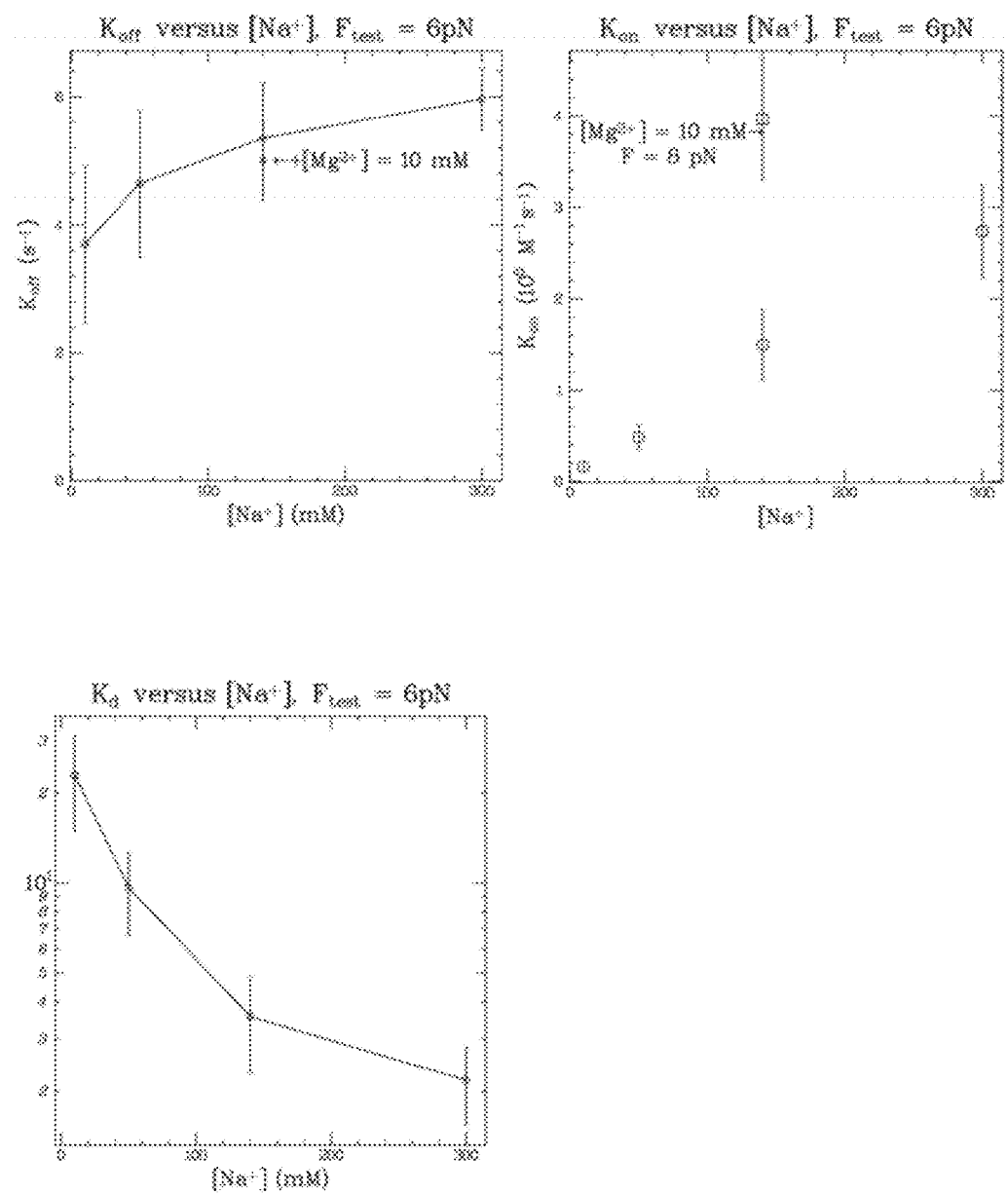

FIG. 5: Kinetics parameters defining the binding property of a 12 nts oligonucleotide to its complementary substrate as a function of the ionic strength of the buffer. $k_{off}$ varies little with the ionic strength while $k_{on}$ present a strong dependency. $k_{on}$ is increased by a factor 3 by adding $Mg^{2+}$. The equilibrium constant $k_d$ can be computed from both kinetic parameters.

Figure 6:
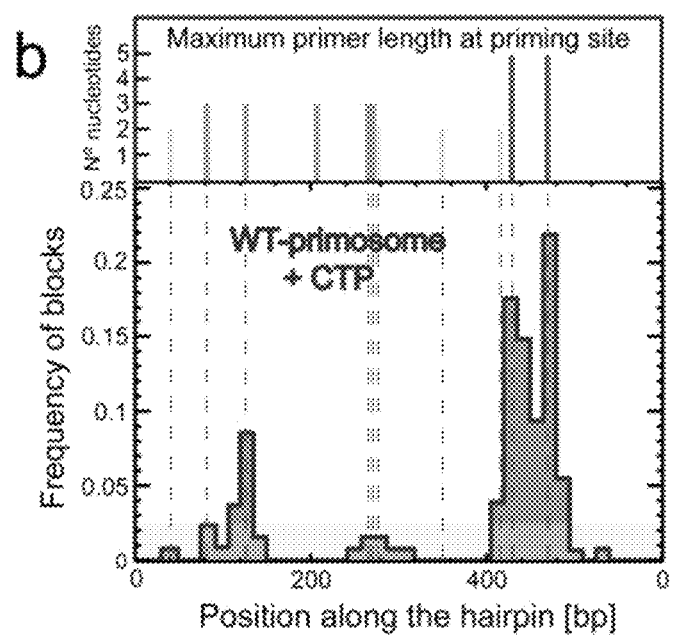
Figure 6:
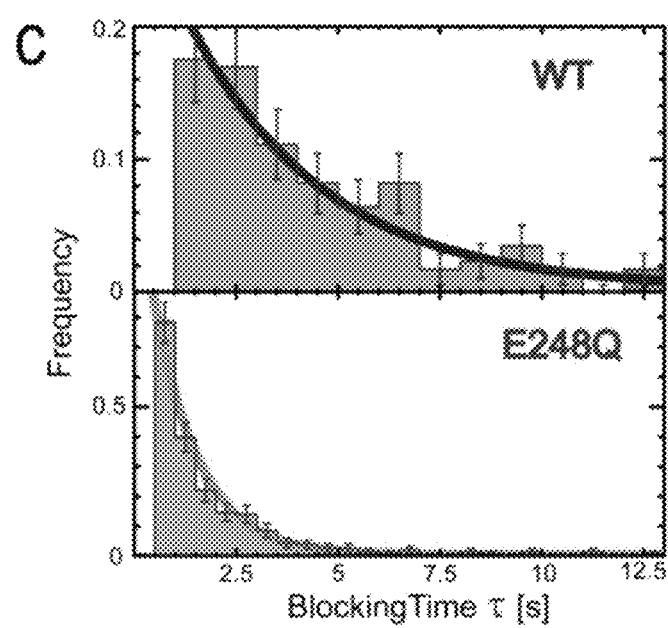

FIG. 6: Blockage of a hairpin by a primase stabilizing a 5 nt-RNA oligonucleotide complementary to priming DNA sequence. b) Position of the blocking event along the sequence. c) Distribution of the blocking time produced by the T4 primase stabilizing a pentamer RNA oligonucleotide in the priming process observed with $F_{test}$=9 pN. The 5 nt-RNA oligonucleotide does not block the hairpin refolding in a visible manner. With the T4 primase WT, the blocking occurs at the expected position along the sequence and the blocking time is 5 s. With the E248Q mutant, we observe the same phenomenon but the blocking time is significantly reduced.

Figure 7:
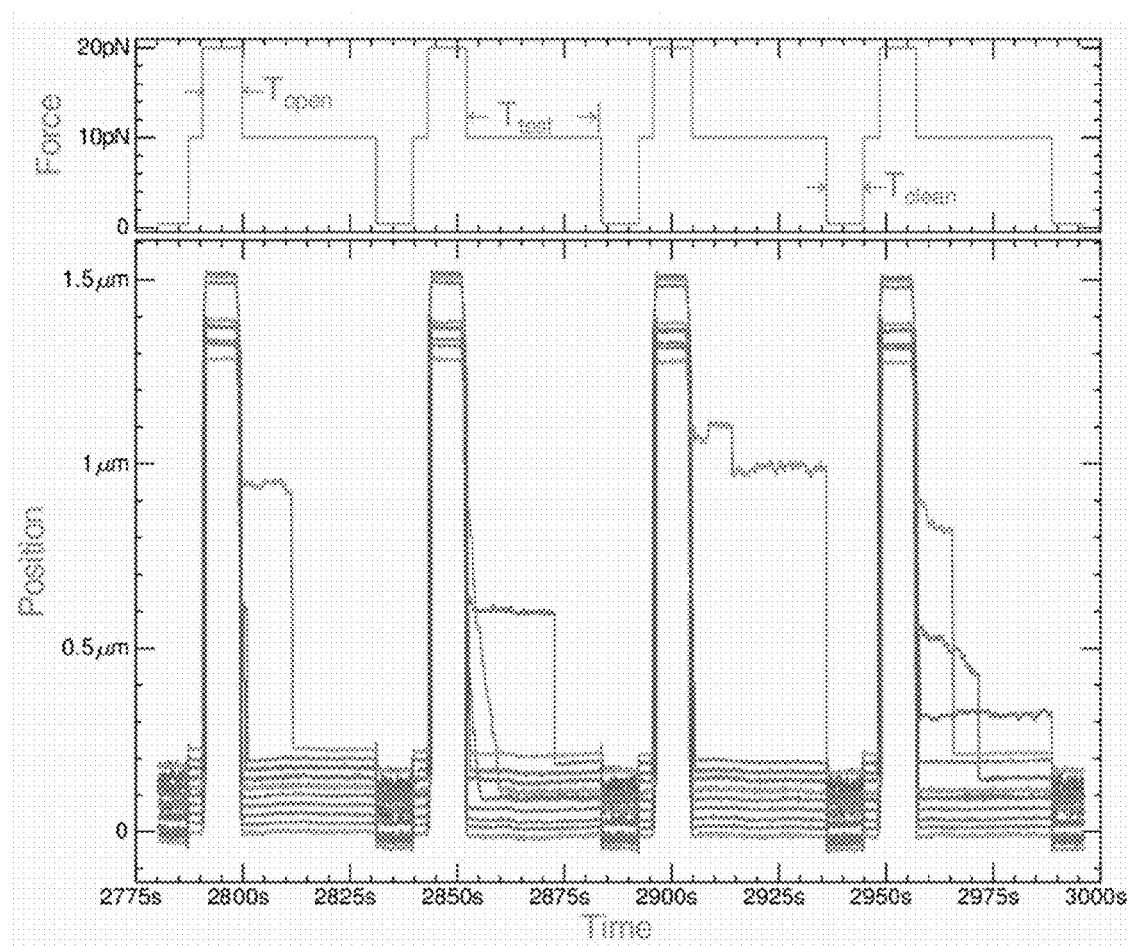

FIG. 7: Series of cycles testing the helicase RecQ binding to ssDNA with three phases: open at $F_{open}$=20 pN, test at $F_{test}$=10 pN and a cleaning phase at $F_{clean}$=0.5 pN. 10 traces are shown with a few presenting a blocking event for one cycle. The cleaning phase at low force insures that any enzyme bound is removed from the template. In the absence of ATP, RecQ just binds and blocks the re-folding, the pressure of the refolding fork produces a sliding of the helicase the blockage position decreasing by successive steps.

Figure 8:
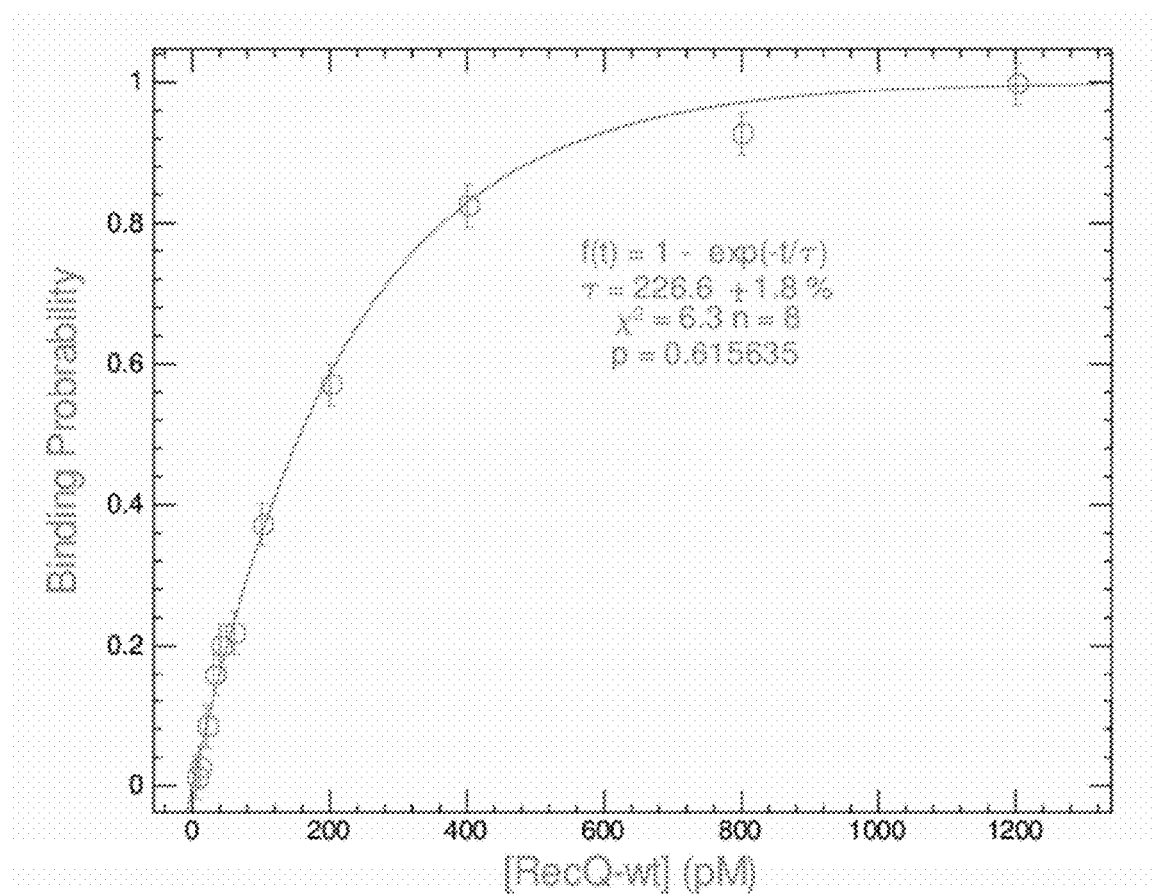

FIG. 8: Evolution of the blocking probability of RecQ versus its concentration. $P_{block}$ increases and saturates as the concentration increases, this defines a characteristic concentration here of 226 pM.

Figure 9:
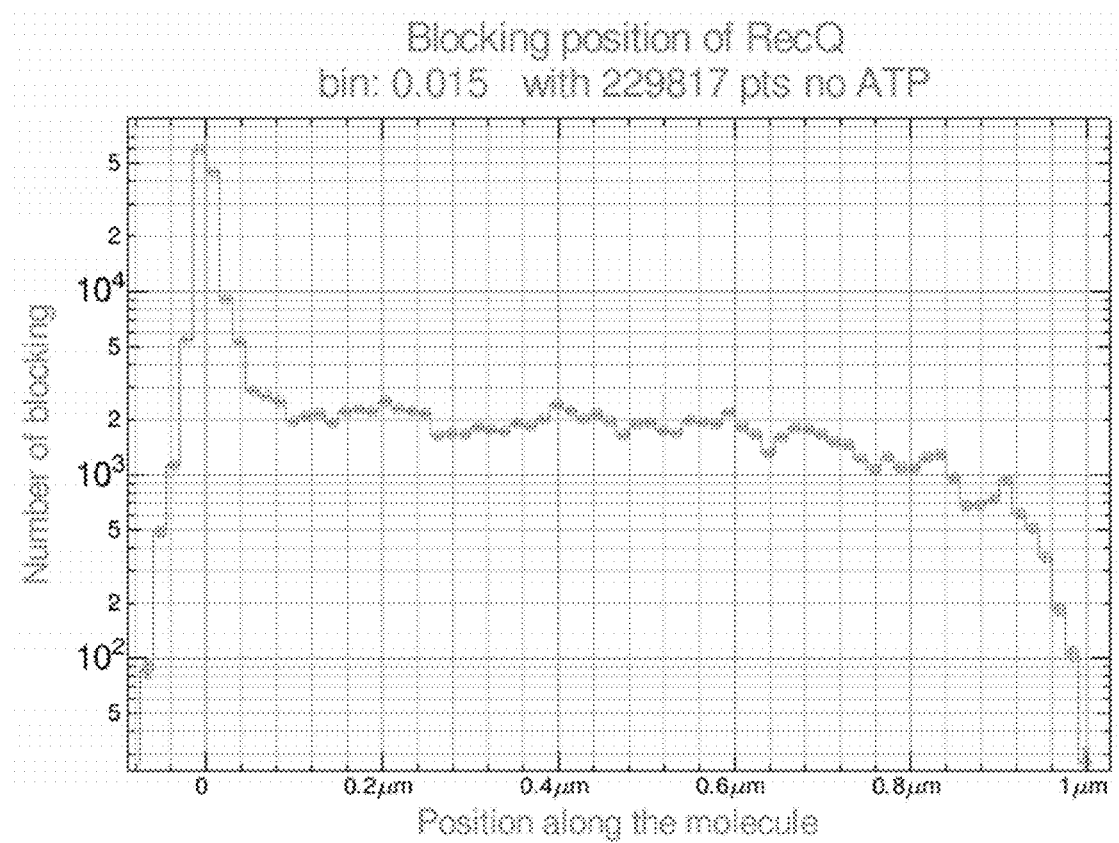

FIG. 9: Distribution of the blocking position of the RecQ helicase without ATP along the template.

Figure 10:
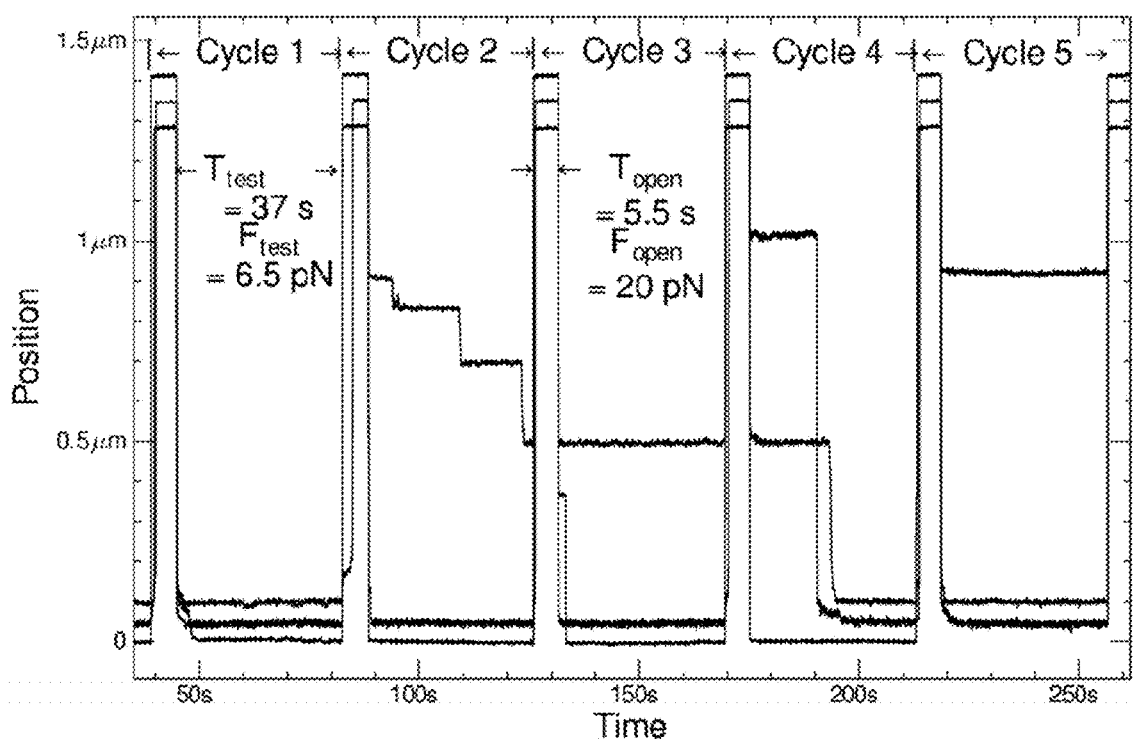

FIG. 10: Raw signal of the blockage produced by the antibody against methylation Cytosine along a 1.2 kb DNA hairpin. Three traces displayed the extension of hairpins over 5 cycles. Each cycle starts by opening the hairpin for 5.5 s with a force of 20 pN followed by the test phase lasting 37 s at F=6.5 pN.

Most of the time the cycle do not present blockage (1), one hairpin may present successive blockage during the same cycle (2) and the blockage can extend over several cycles. [Ac] the antibody concentration is 35 nM, the buffer is Tris 100 mM with 0.2% of BSA to prevent non-specific binding.

Traces have been shifted in y for clarity.

Figure 11:
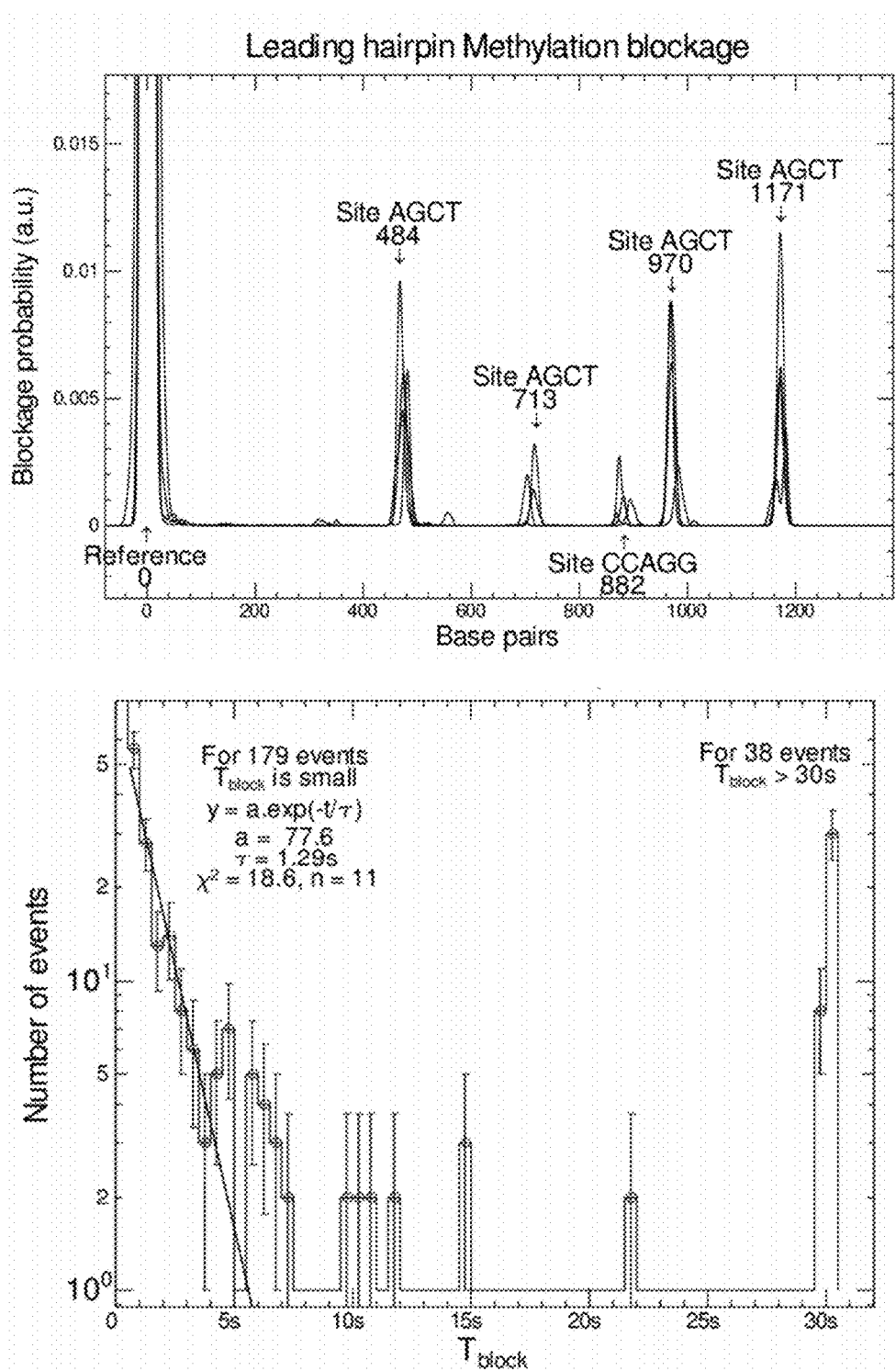

FIG. 11: Histogram of the methylation position along the sequence of a 1.2 kb hairpin after it has been methylated by a human DNA methyl-transferase. Four histograms of different beads are displayed. There is a consensus on the binding positions; we observe the four expected binding positions related to the eukaryotic methylation as well as the one in 882 corresponding to the methylation done by E. coli where the DNA was originally produced.

Figure 12:
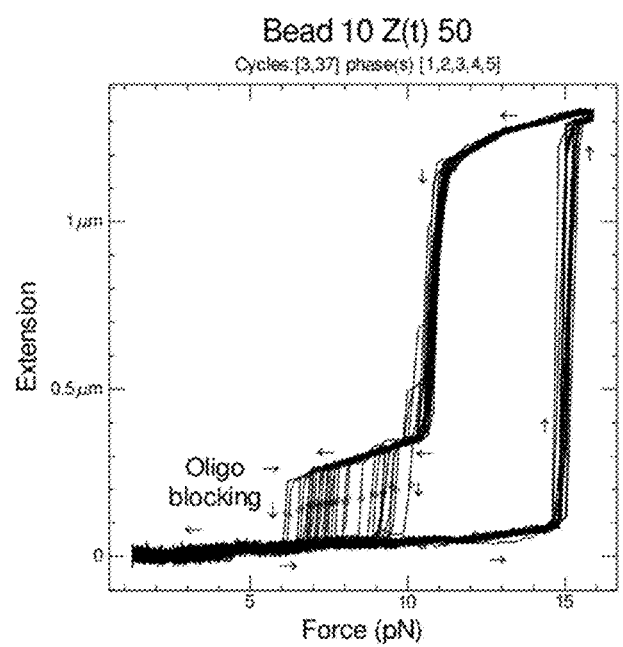
Figure 12:
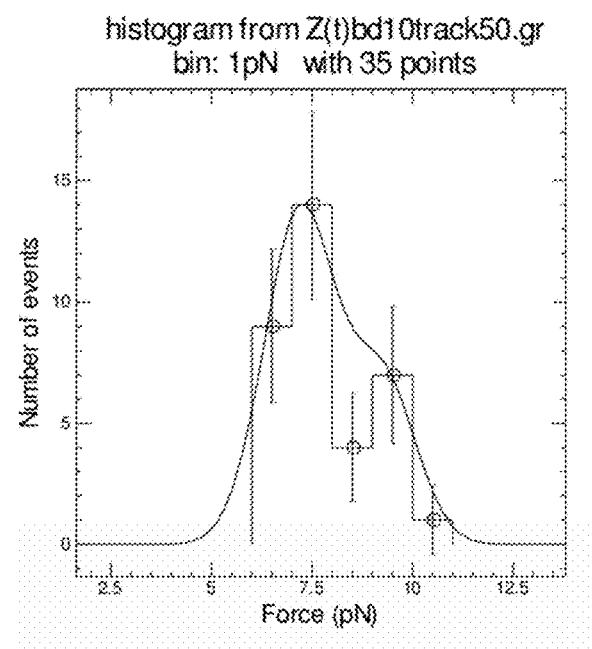

FIG. 12: Recording of 30 cycles of opening and closing the hairpin with a smooth ramp in force with 2 s to go up and 2 s to go down. The representative points in the cycle turn counter clockwise (see arrows) starting at F=1.5 pN and Z=0; as the force increases the extension remains very small until the force reaches 15 pN, there the molecule opens and Z reaches 1.3 µm. When the force is decreased with a ramp, Z slowly decreases until F=11 pN at this point the hairpin refolds until it bumps in the 12-nt oligonucleotide. As the force continue to decrease so does the Z of blocking but as the force decreases it soon reaches the point where the oligonucleotide is expelled as seen by the rapid decrease in Z mark by a diamond symbol. The distribution of force corresponding to the oligonucleotide detachment is displayed on the right; its maximum around 7 pN corresponds to the force at which $T_{off}$ equals a fraction of a second.

Figure 13:
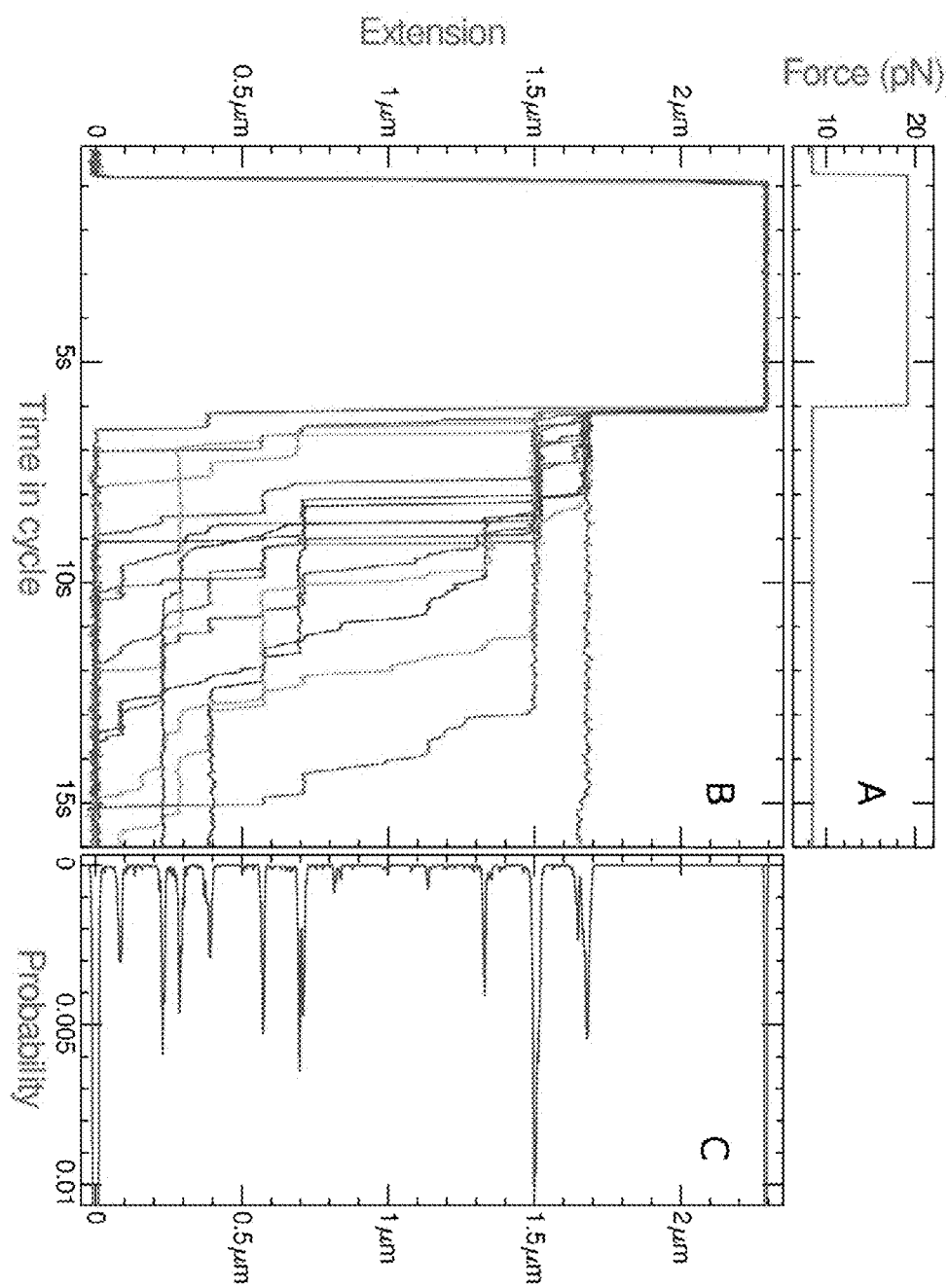

FIG. 13: Detection of methylation sites on a human DNA obtained from human cells. A hairpin DNA was prepared from a 2.5 kb human genomic DNA molecule. A) Variation of the force applied throughout the measurement cycles: the hairpin is opened for 5 seconds by a 19 pN force; the force is then reduced to 8.5 pN for 10 seconds. B) Superposition of the signals obtained on ca. 20 cycles in presence of antibodies directed against 5mC, showing the unzipping of the molecule, followed by its rezipping interrupted by transient blockages. These blockages are caused by the binding of the antibody to 5mC. C) A histogram of the blockages positions shows well-defined positions corresponding to the presence of 5mC. There are about 20 positions, which suggests a methylation every ca. 100 bases.

EXPERIMENTAL EXAMPLES

Binding of protein to DNA is a major phenomenon in biology; it is a very general process which control many reactions. While the thermodynamical equilibrium properties of this mechanism are well known, measuring its kinetics is a more challenging problem. Using single molecule offers the ability to measure the time required for a protein to find its DNA target but also the accurate location of the binding event. We describe here a new single molecule assay achieving these goals.

Although the assay is broad we illustrate first its applicability to the binding of a specific oligonucleotide, and to the non-specific binding of an helicase to ssDNA. Finally we discuss the specific binding of an antibody recognizing methylated sites in DNA.

This invention concerns a novel process for detection of a wide variety of DNA modifications and DNA-protein binding events based on the mechanical detection of the obstruction of re-hybridization of a DNA hairpin. The assay relies on a series of cycles providing statistical information of single molecule binding. During one cycle, one starts by an unzipping phase where a single DNA hairpin is unfold during a time $T_{open}$ by pulling on its extremities with a force $F_{open}$ larger than about 16 pN. In a second test phase lasting $T_{test}$ the tension $F_{test}$ is reduced to below about 11 pN allows for the hairpin to re-zip. If a molecule present in solution can bind to a definite sequence or non-specifically on the open hairpin (e.g. a protein capable of recognizing a specific single or double strand sequence, modified or not), it will bind to the DNA with a probability $P_{block}$ and, in that event, will transiently block its re-zipping when the force is reduced below about 11 pN. This obstruction is easily detectable as a pause occurring at a definite position during re-hybridization of the hairpin which leads to three parameters:

the position $z_{block}$ of this pause along the stretched DNA is characteristic of the sequence being recognized;

the duration of the blockage $T_{off}$ characterizes the time during which the molecule has remained bound to DNA; and the probability of blockage $P_{block}$ which is related to the time $T_{on}$ required for the molecule to find its binding site.

$T_{on}$ and $T_{off}$ are both characteristic of the strength of the interaction between the DNA and the blocking molecule. Thus by probing with a methylation recognizing protein or antibody a DNA sequence (bound as a hairpin to a bead at one end and to a surface at the other), one can identify by repeated cycles of opening and closing of the hairpin the presence of the probed methylation site (via the presence of a blockage of some of the hairpins during re-hybridization). One can similarly measure the binding of a protein to a putative dsDNA site by measuring the increase in the stability of the hybrid between a complementary oligonucleotide in presence vs. absence of the protein.

This invention allows for detection of DNA modifications on genomic DNA without passing through bisulfite reaction and PCR amplification steps. It requires some pre-processing of the DNA necessary to process it into hairpin fragments that can be used to bind beads to a surface (fragmentation and ligation with adequate fragments). The present invention does not require fluorescent Labeling of the proteins or DNA. In its present realization, the technique necessitates an optical (microscope) to detect the blockage of the hairpin during re-hybridization.

A double-strand (ds) DNA fragment of a size comprised between a few tens and a few thousands base-pairs (obtained for example from mechanical shearing or restriction cuts of genomic DNA) is ligated at one of its extremities to a DNA loop. Its other extremities are ligated to a dsDNA fragment allowing for the binding of its two strands to differently coated surfaces. For example the free 3' end of one strand can be labeled with biotin allowing binding to streptavidin coated beads, whereas the 5' end on the opposite strand can be labeled with digoxigenin allowing its binding to surfaces coated with an anti-Dig antibody. This end-labeling can be done by various ways known to the man of the art, such as the use of terminal transferase to add biotin (or dig) modified nucleotides or hybridization with suitably labeled oligo-nucleotides.

This DNA construct is incubated for a few minutes in a solution of adequate beads (for example streptavidin coated ones) to which it binds by one of its labeled (for example biotin) ends. The beads can be transparent if optical tweezers are later used for manipulation or magnetic if one uses magnetic traps or tweezers for manipulation.

The bead-DNA assembly is injected in a fluidic chamber, the surface of which has been treated such as to bind the other labeled end of the molecule (for example a surface coated with anti-Dig to bind the Dig-labeled end of the DNA). The beads are thus anchored to the surface via a DNA-hairpin (see FIG. 1a below). The distance of the bead to the surface is then monitored by various means. For example the diffraction rings of the bead image on a camera can be used to deduce their distance.

The light intensity scattered by the beads (or emitted as fluorescence) when illuminated in an evanescent mode could also be used to measure their distance. Alternatively, when using magnetic beads, the magnetic field generated can be measured (using GMR or Hall sensors) to deduce the bead-surface distance to a sensor on the anchoring surface.

To pull on the DNA molecule anchoring the beads to the surface various techniques have been described. One can use the light of a focused laser beam to trap a transparent bead near the focal point. By the relative translation of the beam with respect to the anchoring surface one can apply a force on the tethering molecule (a typical optical tweezers assay). The exerted force being proportional to the displacement of the bead from its equilibrium position, to exert a constant force on the tethering molecule requires a feedback Loop on the trapping beam.

To exert a constant force on a bead, the use of the hydrodynamic drag generated by a flow around the bead has been described, but it usually yields a low spatial accuracy (>100 nm). The preferred embodiment uses magnetic trap to pull on super-paramagnetic beads anchored to a surface by a DNA hairpin as described above. In this configuration, small magnets placed above the sample are used to apply a constant force on the anchored bead, whose position can be determined with ~1 nm accuracy (depending on the pulling force and the dissipation due to hydrodynamic drag).

In every case one notices that the tethering hairpin can be mechanically unzipped fully by pulling on the beads with a force larger than about 16 pN. Reducing the tension on the molecule below ~11 pN allows the hairpin to re-zip spontaneously (the unzipping transition is reversible though hysteretic).

If, during the unzipped phase, some molecules in solution (such as proteins and/or complementary oligonucleotides of DNA, RNA, LNA or PNA) have bound to the stretched single stranded (ss) DNA, these molecules will transiently block the re-zipping of the hairpin when the force is lowered to below ~11 pN.

By measuring the extension of the DNA molecule Z(t) (the distance of the bead to the surface) over a series of cycles during one of these rezipping pauses, one can determine the position of the blockage with an approximately 1 nm precision (which corresponds to the distance spanned by two nucleotides (1 bp) in a ssDNA under a 10 pN force). Moreover, by measuring the mean time of blockage one can determine $T_{off}=1/k_{off}$. By measuring $P_{block}$ and knowing the molecule concentration [M], it is possible to gain access to $T_{on}$ and thus $k_{on}$. One or both of these parameter help to characterize the binding nature. It is possible, for instance, to determine if it is due to a perfect hybridization with a complementary oligo-nucleotide or not, or if a protein stabilizes the hybridization or not, and if there is a mismatch and where is it (for example at the center of the hybridized oligonucleotide or near one of its ends).

These observations suggest various realizations for applications in the detection of DNA modifications and more generally in the detection of the interaction of proteins with ss or dsDNA.

Detection of DNA Modifications by Mechanical Detection of Blockages During Rehybridization.

If oligonucleotides (of Length larger than seven nucleotides) are present in solution when the DNA hairpin is mechanically unzipped, these oligonucleotides can pair with their complementary sequence on the DNA and transiently prevent the full re-zipping of the hairpin when the force is lowered below 11 pN, see FIG. 1b. One can easily perform a series of unzipping/re-zipping cycles on the same molecule and detect the blockages (pause) upon re-zipping due to pairing of oligo-nucleotides with a DNA in the unzipped phase.

The blocking time duration presents typically an exponential distribution which mean value $T_{off}$ which decreases exponentially with $F_{test}$. This probability distribution is reminiscent of the single molecule nature of this assay. It has some consequences: the most probable blocking time is 0 which means that there exists a substantial fraction of blockage that we shall not detect because they are shorter than our experimental resolution. The molecule blocking the hairpin refolding is under the pressure off the DNA fork. If $F_{test}$ is close to 15 pN the (mechanical hairpin unfolding force), this pressure is weak, on the contrary if $F_{test}$ is reduced, the fork pressure increases drastically expelling the molecule. We find that $T_{off}$ decreases exponentially with $F_{test}$ as shown on FIG. 2. This dependency is so strong that we can only measure $T_{off}$ in a range of a few pN. Notice also that $T_{off}(F)$ would only coincide with the classical $T_{off}$ of a molecule unbinding spontaneously when $F_{test}=F_{unzip}=15pN$ which is not achievable here.

The blocking probability $P_{block}$ increases with the duration of the open phase $T_{open}$ with an exponential behavior: $P_{block}=a(F)\cdot[1-\exp(T_{open}/T_{on})]$ as shown in FIG. 3.

As one may expect $P_{block}$ increases with the concentration of the molecule, in FIG. 4 we show that for a 12-nt oligonucleotide, $P_{block}$ increases and saturates with [M].

Knowing $T_{open}$ and the molecule concentration [M], it is possible to deduce kon from $P_{block}$ using the following relation:

$$k_{on}=-\text{Log}(1-P_{block}/a(F))/([M]T_{open}).$$

The strength of the binding (see FIG. 5) can be characterized by:

$$k_d^{-1}=-(T_{off}\text{Log}(1-P_{block}/a(F))/([M]T_{open})$$

The mean time of blockage $T_{off}$ depends on the size of the oligo-nucleotide, the force $F_{test}$ applied during rezipping, the temperature and not significantly from the ionic strength of the buffer used.

The $T_{on}$ depends also on the size of the oligonucleotide of the temperature, of the ionic strength of the buffer but not significantly on $F_{test}$. As shown in FIG. 5, mismatches between the oligonucleotide and the substrate can also be characterized by measuring these kinetics constants. For instance, a fully complementary 12 nts oligonucleotide presents a $k_{on}$ of $1.5\times10^{-6}M^{-1}s^{-1}$, introducing a single mismatch 3 bases away from one end does not alter much $k_{on}$.

Moving the mismatch in the middle of the oligonucleotide reduces $k_{on}$ by a factor 10.

$T_{off}$ also depends on the presence of dsDNA binding proteins that may stabilize the hybrid. For example we have shown that a primase will stabilize DNA oligos that would not otherwise have been sufficiently stable to block the hairpin re-hybridization for a time long enough to be detected, see FIG. 6. In a similar manner, the binding of a polymerase to the 3' end of a small oligonucleotide used as a primer will increase its stability; this assay can be used to determine the affinity of the polymerase to its primer site. Similarly if a protein binds to a specific ssDNA site (for example a methylated base) it will block re-zipping at a specific site and for long enough to be detected.

The technique can be used to identify DNA modifications along a ss or dsDNA. Thus by probing the DNA hairpins anchoring the beads to the surface with an antibody (Ab) directed against a specific modification of one of its bases, one can detect the existence and position of this modified base along the chain via the transient blockage that will result from the Ab binding upon re-hybridization of the hairpin. Probing the binding site with a set of complementary oligo-nucleotides will allow for the identification of the DNA fragment exhibiting that modification.

Detection of the Binding Affinity of RecQ to a ssDNA Template.

Helicases binds to ssDNA gaps in order to unwind dsDNA. The activity of these enzymes is directly dependent of its affinity to ssDNA. We propose here to measure this parameter directly with or assay. This can be done with or without ATP or ADP or other analogues. We present here some results concerning the RecQ helicase from E. coli without ATP. The typical binding signal can be seen on FIG. 7, it allows to measure $P_{block}$ for one helicase concentration. The evolution of $P_{block}$ versus [RecQ] is displayed on FIG. 8. We observe that the characteristic concentration of [RecQ] equals 226 pM. In FIG. 9, we see that the helicase binds non-specifically. Finally, the blockage by the enzyme displays slippage behavior: the Z position is not really constant but decrease by multiple steps. With this behavior, it is difficult to define a real value of $T_{off}$ and thus we can only measure $T_{on}$ and $k_{on}$.

The peak at Z=0 does not correspond to a blockage but just to the direct refolding. RecQ blockage is found uniform along the template, the decay at 0.9 μm is due to the averaging of molecules having slightly different extension.

Detection of Methylation

FIG. 11: Histogram of the blockage time by the antibody against 5mC. Most of the blockage are short and can be reasonably well fitted to an exponential distribution with a characteristic time of 1.3 s. However a substantial number of blockage 17.5% exceeds 30 s. In this condition it is not very easy to determine the $T_{off}$ of the enzyme, we believe that two different binding mechanisms are competing with one more stronger than the other.

Alternatively one can probe for the existence of known DNA modifications by hybridization of an oligonucleotide complementary to the putative modified site in presence (or not) of a protein that recognizes the modification (such as the methyl binding domain protein 1 (MBD1) that recognizes methylated cytosines or an appropriate Ab raised against a specifically modified dsDNA). The blockage time in presence of the protein will be significantly increased leading to an easy identification and location of the modified base.

By using mismatch-recognizing proteins one could similarly use the aforementioned method to identify mismatches (i.e. SNPs) along the DNA. One may also use that assay to detect proteins (or drugs) that will affect the stability of a given protein/DNA complex.

Parameters Influencing the Assay.

$F_{open}$: a 20 pN value is a good choice because this insure that a large number of beads will simultaneously open (their magnetization and thus their force varying by 10 to 20%).

$T_{open}$ appears as an important parameter in combination with the molecule concentration: to observe blockage one must use a combination of both parameter leading to a substantial value of $P_{block}$ according to the formula:

$$P_{block}=a(F)\cdot[1-\exp(T_{open}\cdot k_{on}\cdot[M])].$$

If one wants to measure $k_{on}$, it is judicious to avoid saturating $P_{block}$, adjusting [M] and $T_{open}$ to achieve a $P_{block}$ in the range 0.2 to 0.5 will insure a minimum number of cycles to achieve reasonable statistics. Notice that $T_{open}$ can be modified simply by adjusting a parameter in the acquisition program, changing the enzyme concentration requires to change the buffer in the flow chamber. On the other hand if $k_{on}$ is not to be measured it is worth saturating $P_{block}$ this will yield to the best statistics of blockage. The molecule concentration can be limited by its supply or by unwanted binding, for instance in the study using anti-body against 5mC, at high concentration this enzyme binds to the double stranded DNA of the hairpin in its close state preventing its unfolding. We have found that imiting the enzyme concentration below 35 nM solves this issue. In these experiments increasing $T_{open}$ is the only way to increase $P_{block}$.

The parameter a(F) is in principle close to 1, the best way to evaluate its value is to perform a saturating assay varying either $T_{open}$ or [M] until $P_{block}$ asymptotically reaches a(F) as in FIGS. 3 and 4. Alternatively, it is possible to estimate a(F) with the following formula:

$$a(F) = \exp(-T_{dead}/T_{off})$$

wherein $T_{dead}$ is the dead time of the detection system and $T_{off}$ the mean blocking time. Typically $T_{dead}$ is of the order of 0.1 s.

$F_{test}$ is a very important parameter to adjust: its range depends of the hairpin used but typically spans [12 pN, 2 pN]. For force higher than 12 pN the hairpin refolding presents already some blockages due to secondary structure forming the ssDNA which mask interesting signals. At low forces, the extension of DNA becomes very small and the noise increases drastically. The hairpin fork pressure pushes the molecule to de-hybridized very efficiently and we observe that the $T_{off} = T_0 \exp F/F_0$; thus $T_{off}$ decreases very fast as $F_{test}$ is reduced. For instance a 9 nts oligonucleotide will produce a is blockage around $F_{test}$=11 pN, at force below 9 pN the blockage is hardly visible (a(F) becomes small). For a 12 nts oligonucleotide the observation range is [10 pN, 6 pN]. For a 37 nts oligonucleotide, the blockage lasts forever at 6 pN but falls to a few seconds at $F_{test}$=3 pN. The same observation is true for binding protein: the stronger the binding the lower the force at which blockage are observed.

We adjust $F_{test}$ so that the blockage time is measurable (a(F)~1) but not too long so that $T_{test}$ is relatively short allowing many cycles to be made.

In this assay we can measure $T_{off}$ in a range of 0.2 s to 20 s. Shorter time could be observed with a faster measuring device like a fast video camera, Longer time leads to very long acquisition since we need to achieve some cycles to average the distribution. For oligonucleotide, $T_{off}$ varies exponentially with $F_{test}$; thus we can adjust $F_{test}$ to bring $T_{off}$ in the usable range. For protein, the variation of $T_{off}$ with $F_{test}$ is not known but we observe that decreasing $F_{test}$ usually drastically decreases $T_{off}$. However, a priori $T_{off}$ is unknown and may vary in a wide range. To get an idea of the typical value of $F_{test}$ we have found that it is convenient to achieve first a series of cycles with the force rising and decreasing following a ramp over a few seconds as done in FIG. 12. The end of the blocking phase corresponds to a force $F_c$. The distribution of $F_c$ peaks for a value at which $T_{off}$ is of the order of the ramp duration.

One can then proceed with the cycles having plateaus in force ($F_{open}$ and $F_{test}$) with $F_{test}$ slightly larger than $<F_c>$ to obtain a $T_{off}$ in the measurable range.

$T_{test}$ and $N_{cycles}$: $T_{test}$ should be 2 or 3 times larger than $T_{off}$. Finally the number of cycles defines the overall accuracy of the measurement. To achieve a X % accuracy we need $X/100 = 1/N_{block}^{1/2}$ comme $P_{block} = N_{block}/N_{cycle}$; On a $N_{cycle} = 10000/(X^2 P_{block})$.

Improving the assay: various problems arise frequently, the binding of an enzyme may present short and also very long events (FIG. 9); this last situation will result in that the blockage is still active while the end of the test phase and the beginning of the new cycle starts (FIG. 7). Since the blockage is hidden during the open phase, the blockage extending over successive cycles is likely but never a proven event. To avoid this awkward situation, it is possible to take advantage of the fact that blockage are usually very short at low forces. Thus by adding a third phases after the test one with a low force one can clean the hairpin of any bound molecule, with $F_{clean}$=0.5 pN and $T_{clean}$=2 s, we remove any molecule bound and prepare a clean hairpin for the next cycle. A molecule may also present several binding sites and thus the blockage signal will have a staircase appearance where after a first blockage the molecule blocks on the second binding site and so forth (FIG. 10). For the second blockage the effective open phase is $T_{open} + T_{block1}$ (FIG. 10); if $T_{block1}$ is greater than $T_{open}$, you are more likely to observe a second blockage after a first one messing up the measurement of the kinetics parameters. Then it is better to use a large $T_{open}$ compared with $T_{test}$ to minimize this effect.

The invention claimed is:

1. A method for detecting a modified base within a double-stranded nucleic acid molecule, said method comprising the steps of:
   a) providing a nucleic acid hairpin molecule consisting of a double-stranded stem and a single-stranded loop, wherein the 5' and 3' ends of the nucleic acid hairpin molecule are bound to different surfaces;
   b) applying a force to move one of the surfaces away from the other surface, thereby yielding a completely denatured hairpin molecule;
   c) contacting the completely denatured hairpin molecule with an antibody that specifically binds to the modified base;
   d) reducing the force to allow renaturation of the hairpin molecule in the presence of the antibody, wherein the antibody binding to the modified base causes a transient blockage of the renaturation of the hairpin molecule;

e) detecting the transient blockage of the renaturation of the hairpin molecule due to binding of the antibody to the modified base in the hairpin molecule; and f) determining the position of the modified base within the double-stranded nucleic acid molecule by determining the position of the transient blockage.

2. The method of claim 1, wherein the force in step b) is above or equal to 15 pN.

3. The method of claim 1, wherein the force in step b) is above or equal to 17 pN.

4. The method of claim 1, wherein the force in step b) is above or equal to 18 pN.

5. The method of claim 1, wherein the force is reduced in step d) to less than or equal to 12 pN.

6. The method of claim 1, wherein the force is reduced in step d) to less than or equal to 11 pN.

7. The method of claim 1, wherein the force is reduced in step d) to less than or equal to 10 pN.

8. The method of claim 1, wherein one of the surfaces is a magnetic bead.

9. The method of claim 8, wherein the force is a magnetic force.

10. The method of claim 1, wherein steps a) - f) are repeated.

11. The method of claim 1, further comprising measuring the duration of the blockage.

12. The method of claim 1, wherein the modified base is selected from the group consisting of 4-methylcytosine, 5-methylcytosine, 5-hydroxymethylcytosine, 5-formylcytosine, 5-carboxylcytosine, 5-hydroxymethyluracil, and N6-methyladenosine.

13. The method of claim 1, wherein the modified base is 5-methylcytosine.

14. A method for detecting a modified base within a double-stranded nucleic acid molecule, said method comprising the steps of:

a) providing a nucleic acid hairpin molecule consisting of a double-stranded stem and a single-stranded loop, wherein the 5' and 3' ends of the nucleic acid hairpin molecule are bound to different surfaces;

b) applying a force to move one of the surfaces away from the other surface, thereby yielding a completely denatured hairpin molecule;

c) contacting the completely denatured hairpin molecule with a protein that specifically binds to the modified base, wherein the modified base is mismatched with the base on the other strand of the hairpin molecule;

d) reducing the force to allow renaturation of the hairpin molecule in the presence of the protein;

e) detecting blockage of the renaturation of the hairpin molecule due to binding of the protein to the modified base in the hairpin molecule; and f) determining the position of the blockage.

15. A method for detecting a modified base within a double-stranded nucleic acid molecule, said method comprising the steps of:

a) providing a nucleic acid hairpin molecule consisting of a double-stranded stem and a single-stranded loop, wherein the 5' and 3' ends of the nucleic acid hairpin molecule are bound to different surfaces;

b) applying a force to move one of the surfaces away from the other surface, thereby yielding a completely denatured hairpin molecule;

c) contacting the completely denatured hairpin molecule with a protein that specifically binds to the modified base, d) reducing the force to allow renaturation of the hairpin molecule in the presence of the protein;

e) detecting blockage of the renaturation of the hairpin molecule due to binding of the protein to the modified base in the hairpin molecule; and f) determining the position of the blockage;

wherein the protein is selected from the group consisting of a MutS dimer, Msh2/Msh6, and Msh2/Msh3, and wherein the method further comprises hybridizing a single-stranded nucleic acid that has a mismatch with the completely denatured hairpin molecule prior to step c).

* * * * *

SEQUENCE LISTING

<160> NUMBER OF SEQ ID NOS: 1

<210> SEQ ID NO 1
<211> LENGTH: 12
<212> TYPE: DNA
<213> ORGANISM: Artificial Sequence
<220> FEATURE:
<223> OTHER INFORMATION: Oligonucleotide

<400> SEQUENCE: 1
acagccagcc ga                                                        12